(12) United States Patent
Beach et al.

(10) Patent No.: US 8,728,414 B2
(45) Date of Patent: May 20, 2014

(54) CLOSURE, CONTAINING APPARATUS, AND METHOD OF USING SAME

(75) Inventors: Michael Beach, Fitzroy Harbour (CA); Roy Sunstrum, Richmond (CA); Maurice Lavimodiere, Midhurst (CA); Adele Jackson, Stittsville (CA); Rafal Michal Iwasiow, Ottawa (CA); Ellen Maclean, Kanata (CA); H. Chaim Birnboim, Ottawa (CA)

(73) Assignee: DNA Genotek Inc., Kanata (CA)

( * ) Notice: Subject to any disclaimer, the term of this patent is extended or adjusted under 35 U.S.C. 154(b) by 83 days.

(21) Appl. No.: 13/320,491

(22) PCT Filed: May 14, 2010

(86) PCT No.: PCT/CA2010/000748
§ 371 (c)(1), (2), (4) Date: Nov. 14, 2011

(87) PCT Pub. No.: WO2010/130055
PCT Pub. Date: Nov. 18, 2010

(65) Prior Publication Data
US 2012/0061392 A1    Mar. 15, 2012

Related U.S. Application Data

(60) Provisional application No. 61/178,311, filed on May 14, 2009.

(51) Int. Cl.
*C12Q 1/68* (2006.01)

(52) U.S. Cl.
USPC .......... 422/550; 422/405; 422/406; 422/547; 422/549; 422/568

(58) Field of Classification Search
USPC ......... 422/401, 405, 406, 547, 549, 560, 561, 422/550, 568
See application file for complete search history.

(56) References Cited

U.S. PATENT DOCUMENTS

| 4,200,100 | A |   | 4/1980 | Willis |         |
|-----------|---|---|--------|--------|---------|
| 5,091,316 | A | * | 2/1992 | Monthony et al. | 600/572 |
| 5,380,492 | A |   | 1/1995 | Seymour |        |
| 5,830,154 | A | * | 11/1998 | Goldstein et al. | 600/572 |

FOREIGN PATENT DOCUMENTS

| GB | 725784 A | 3/1955 |
|----|----------|--------|
| JP | 2-42972  | 2/1990 |

(Continued)

OTHER PUBLICATIONS

The International Search Report mailed on Aug. 26, 2010 for Application No. PCT/CA2010/000748.

(Continued)

*Primary Examiner* — Jill Warden
*Assistant Examiner* — Dwayne K Handy
(74) *Attorney, Agent, or Firm* — Edwards Wildman Palmer LLP; David G. Conlin; Lisa Swiszcz

(57) ABSTRACT

A closure for a container has a closure body having a first cylindrical portion and a second cylindrical portion opposite the first portion. The closure also has a connector disposed in at least one of the first and second portions. The connector is adapted to connect one of a sample collection device and an applicator to the closure. A containing apparatus including the closure, a container, and optionally one of a sample collection device and an applicator is also disclosed. A method of using the containing apparatus is also disclosed.

31 Claims, 17 Drawing Sheets

(56) References Cited

FOREIGN PATENT DOCUMENTS

| JP | 5-94765 | 12/1993 |
|---|---|---|
| JP | 11183468 A | 7/1999 |
| JP | 2004222795 A | 8/2004 |
| JP | 2006115983 A | 5/2006 |
| WO | WO2005/090189 A1 | 9/2005 |

OTHER PUBLICATIONS

Notification of Transmittal of the International Search Report dated Aug. 26, 2010 for Application No. PCT/CA2010/000748.

The Written Opinion dated Aug. 20, 2010 for Application No. PCT/CA2010/000748.

The Response to the Written Opinion dated Sep. 27, 2011 for Application No. PCT/CA2010/000748.

The International Preliminary Report of Patentability dated Sep. 30, 2011 for Application No. PCT/CA2010/000748.

The Examination Report for New Zealand Patent Application No. 596539 dated Oct. 2, 2012.

Patent Examination Report No. 1 for Australian Patent Application No. 2010246874 dated Sep. 10, 2013.

Notice of Reasons for Rejection dated Nov. 26, 2013 for corresponding JP application No. 2012-510084.

Office Action from corresponding Chinese Patent Application No. 201080025278.4, mailed on Jan. 26, 2014.

\* cited by examiner

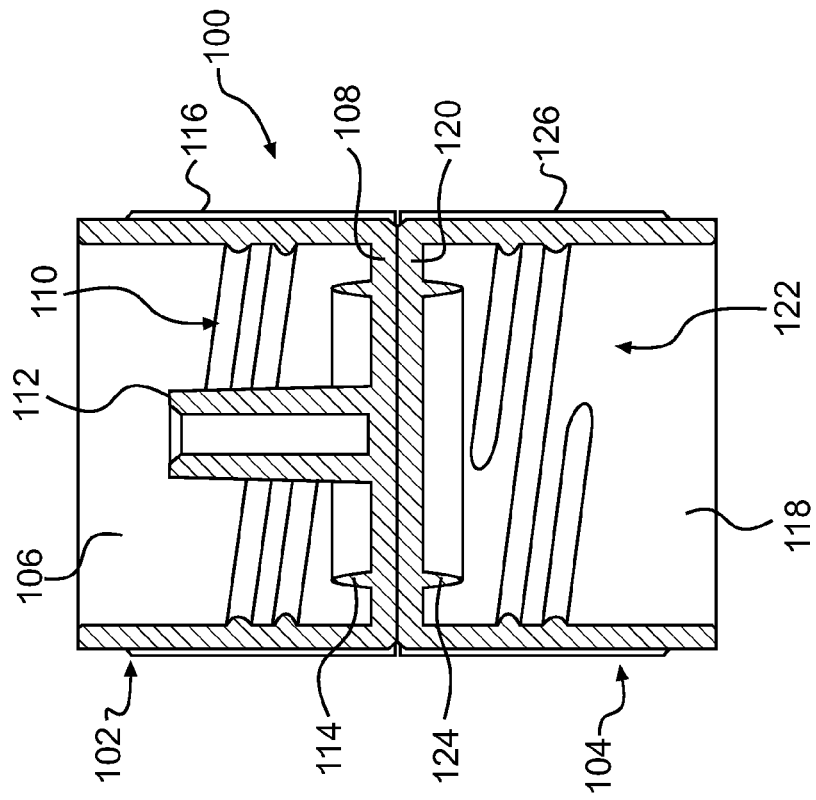
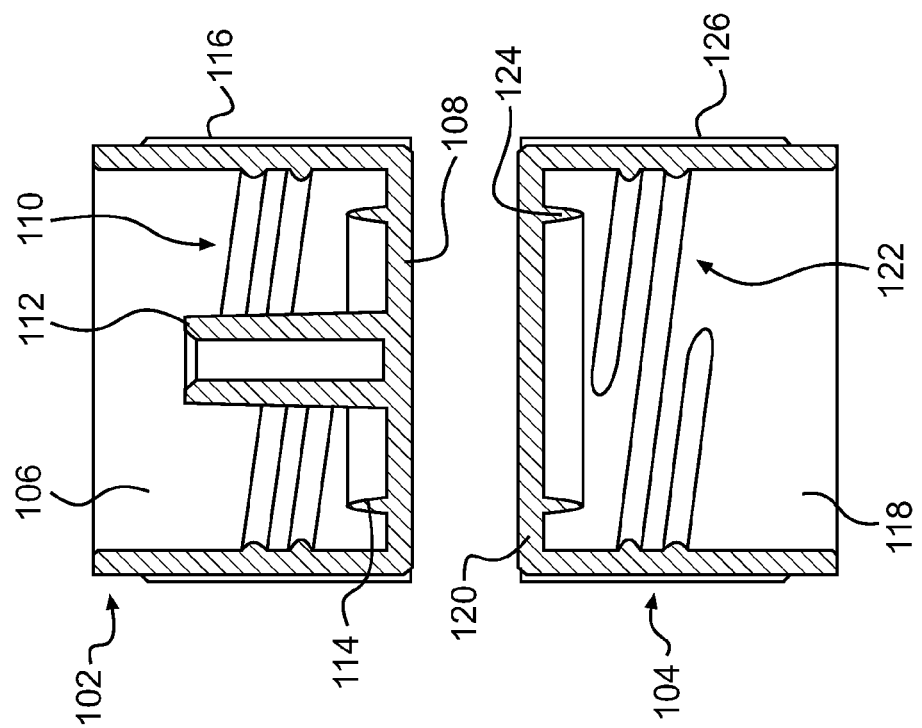

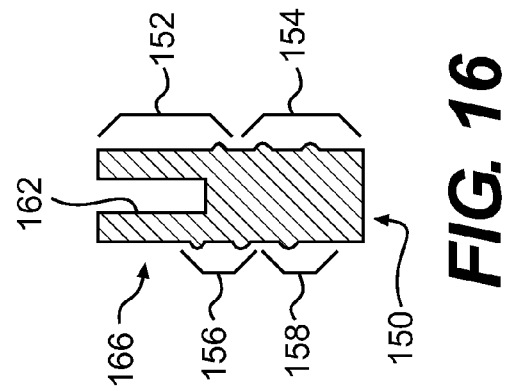
FIG. 16
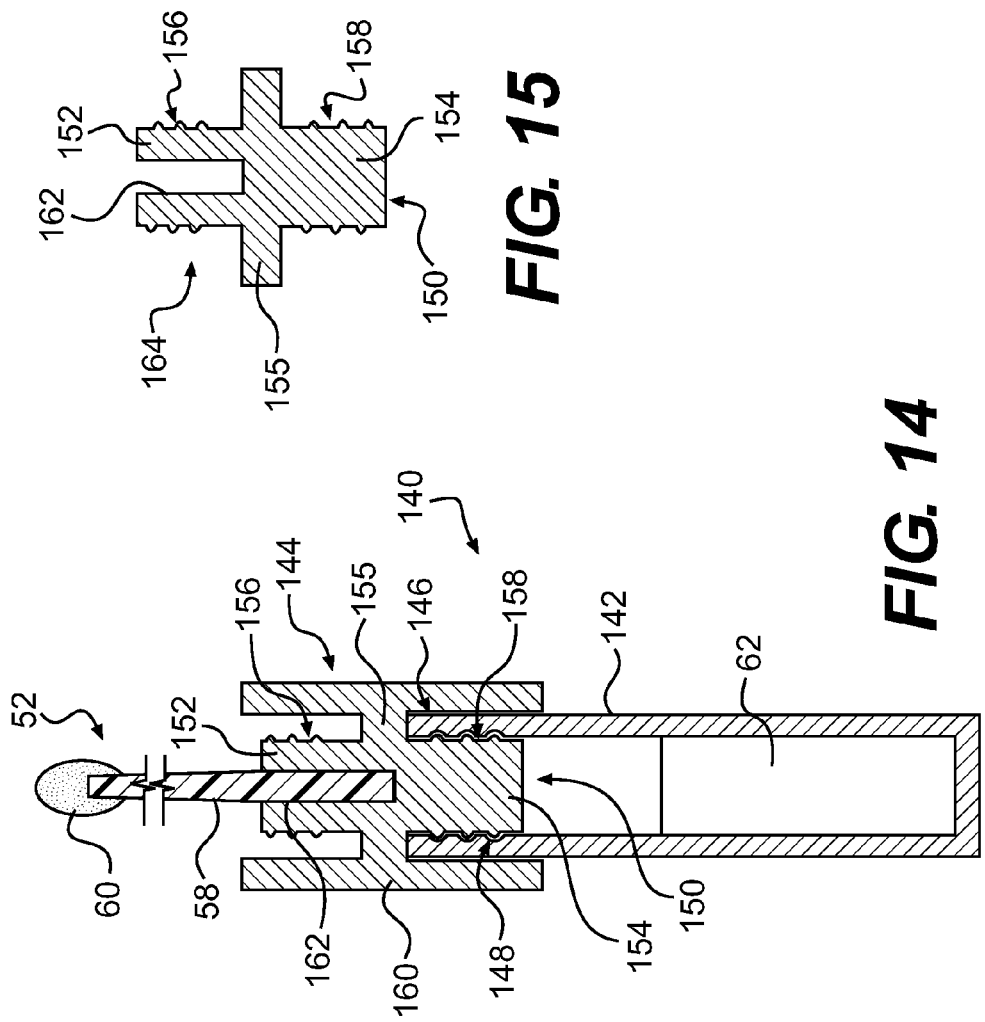
FIG. 15
FIG. 14

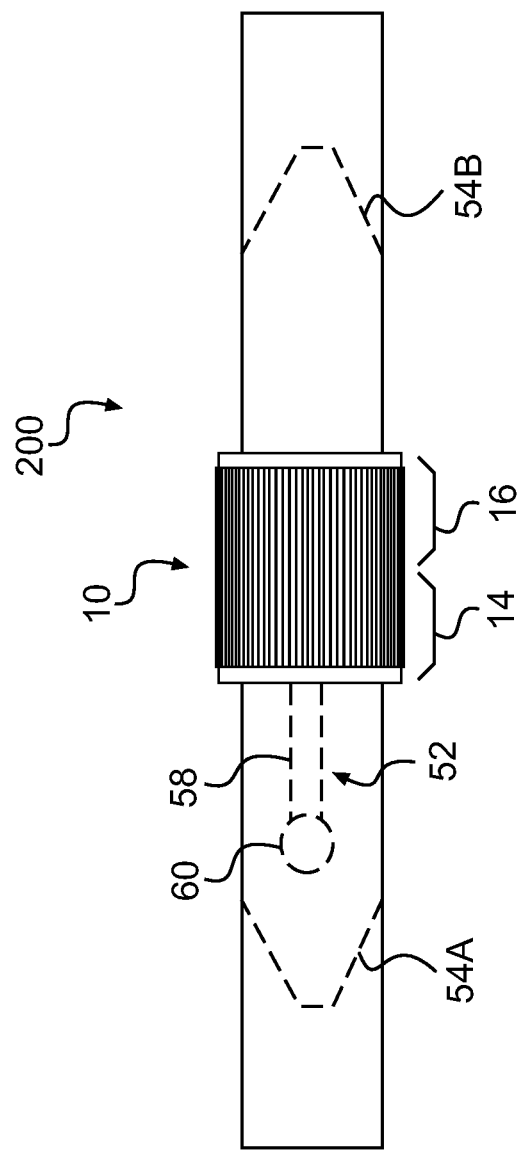

CLOSURE, CONTAINING APPARATUS, AND METHOD OF USING SAME

CROSS-REFERENCES TO RELATED APPLICATIONS

The present application is the 35 U.S.C., §371 national stage of PCT application PCT/CA2010/000748, filed May 14, 2010, which claims priority to U.S. provisional patent application No. 61/178,311, filed May 14, 2009, the entireties of all of which are incorporated by reference herein.

FIELD OF THE INVENTION

The present invention relates to a closure for a container, a containing apparatus using same, and a method of collecting a sample.

BACKGROUND OF THE INVENTION

Collection devices are a type of cap and container combination commonly used for receiving and storing biological samples for delivery to clinical laboratories, where the samples may be analyzed (e.g., to determine the existence or state of a particular condition or the presence of a particular infectious agent, such as a virus or bacterial microorganism, or to perform genotyping, such as for livestock traceability), banked, and/or archived. Since samples can contain pathogenic organisms, it is important to ensure that collection devices are constructed to be substantially leak-proof during transport from the site of collection to the site of analysis. It is also important that the device be substantially leak-proof in order to avoid contamination and maintain the integrity of the sample. This feature of collection devices is especially important when the clinical laboratory and the collection site are remote from one another, increasing the likelihood that the collection device will be inverted or severely jostled during transport and potentially subjected to substantial temperature and pressure fluctuations. Furthermore, it is important that the collection devices are convenient for use by non-technical individuals.

As is known, genotyping and disease detection can be done using biological samples collected from a subject to be tested. In order to perform genotyping and disease detection tests, people typically take venous blood, hair, or tissue samples, but these can be difficult to collect and process. One alternative is to collect biological samples that contain nucleic acids, which are easier to process than the above-mentioned samples and can also be used for genotyping and disease detection. Nucleic acid-containing biological samples include, for example, saliva, sputum, vaginal and nasal mucosal samples. In addition to being easier to process, the procedures for collecting nucleic acid-containing biological fluids tend to be less invasive than taking venous blood, hair, or tissue samples.

Typically collection of biological fluids (other than venous or arterial blood) are easier to collect and more readily accessible and the methods for collection of such biological fluids are less invasive for the donor and less expensive to perform. Highly trained professionals like physicians, phlebotomists and veterinarians are required for the collection of venous or arterial blood and some tissues. An untrained person in an unsupervised setting (e.g., a home, a farm) can collect most biological fluids.

Other biological samples that are routinely collected and stored include, but are not limited to, swabs of potentially contaminated (e.g., by biological agents, radioactive isotopes, etc.) surfaces, biological tissue, such as epithelial cells, tissue plugs or slices (e.g., from carcasses) or geological samples.

One standard method of collecting biological samples involves employing a sample collection device, such as a swab, brush or knife, to the biological sample to be collected and then placing the sample collection device in a stoppered tube. Optionally, the tube may be prefilled with a preserving solution and/or transport medium. The tube is then sent to a laboratory where the nucleic acid contained in the sample can be tested.

This method of collecting the biological samples can however result in the contamination of the sample. Either the stopper needs to be removed prior to applying the sample collection device to the biological fluid, thus increasing the risk of undesirable material entering the tube or coming into contact with the stopper while the sample is gathered, or the sample collection device with the gathered sample needs to be set down while the stopper is removed from the tube, thus increasing the risk of direct contamination of the sample on the swab. To minimize these problems, typically, a second pair of hands and/or a rack/sterile container/bag must be provided, which makes the collection process more complicated and time consuming.

Another source of contamination and cross-contamination is the user's handling of the sample collection device. The user must grip the handle of the swab or other collection device to collect the sample from the source. Even with gloved hands there is significant risk of introducing contaminants to the tube, since the entire swab/collection device is deposited in the tube.

Concerns relating to sample cross-contamination are also inherent to the use of a stopper. Such concerns are especially acute when the sample being collected is to be used in molecular diagnostic techniques employing hybridization and/or amplification of nucleic acids, such as, but not limited to, polymerase chain reaction (PCR), branched chain DNA (bDNA) assays, transcription-mediated amplification (TMA), and reverse transcriptase polymerase chain reaction (RT-PCR). Since amplification is intended to enhance assay sensitivity by increasing the quantity of targeted nucleic acid sequences present in a specimen, transferring even a minute amount of specimen from one container, or target nucleic acid from a positive control sample, to another container can cause confounding or inaccurate results. Similarly, hybridization-based assays may be affected by cross-contamination of samples.

When removing the stopper from the tube or sample collection container, it is possible that some of the preserving solution and/or transport medium could spill due to the pulling motion necessary to remove the stopper. Similarly, after sample collection, if any sample is on the stopper it can spray or spill as the stopper is removed. This is even more likely when the sample collection has to be done by people who are not familiar with such apparatuses, such as a farmer who needs to collect biological samples from his animals for testing or genotyping (e.g., for traceability and parentage).

Additionally, the stopper could leak or become dislodged during transportation from the place where the sample was collected to the laboratory. This problem is made more obvious when the user is an untrained or non-technical person.

Furthermore, it can be difficult to determine if the stopper has been sufficiently pushed into the opening of the container to provide a proper seal.

Additionally, stoppers are often made of rubber, or a similar material, that includes components that can contaminate the biological sample. This can be particularly problematic when the sample is to be used in nucleic acid analysis since components of rubber that can leach into the sample are known to inhibit or interfere with nucleic acid amplification.

Finally, since the sample collection device is essentially loose inside the container once the sample has been collected, automated retrieval of the sample collection device for sample processing is difficult. Therefore, this step is usually performed manually, which can introduce both contamination and cross-contamination of samples.

Therefore, there is a need for an apparatus and method of collecting a sample that reduces the likelihood of contamination of the sample and of leaking or spilling of the preserving solution and/or transport medium prior to and following deposit of the sample.

Furthermore, obtaining samples of animal or human biological sample under farm and/or field conditions is particularly challenging due to the unpredictable behaviour of animals and/or the unsanitary or extreme nature of the farm or field conditions themselves.

Therefore, there is also a need for an apparatus and method for quickly and safely collecting biological samples.

SUMMARY OF THE INVENTION

It is an object of the present invention to ameliorate at least some of the inconveniences present in the prior art.

It is also an object of the present invention to provide a double-ended closure having a connector to connect one of a sample collection device and an applicator such that the sample collection device or the applicator extends from one end thereof. The closure is designed such that either end of the closure can be connected to a container.

It is another object of the present invention to provide a containing apparatus including a container, the above-described closure, and one of a sample collection device and an applicator.

It is yet another object of the present invention to provide a method of collecting a sample using the above-described containing apparatus.

In one aspect, the invention provides a closure for a container. The container has an opened end. The closure has a closure body. The closure body has a first cylindrical portion and a second cylindrical portion opposite the first portion. The closure also has a connector disposed in at least one of the first and second portions. The connector is adapted to connect one of a sample collection device and an applicator to the closure.

In a further aspect, the first cylindrical portion has a first thread region, the second cylindrical portion has a second thread region, and the first and second thread regions are complementary to a thread region of the container located near the opened end of the container for engagement therewith.

In another aspect, the invention provides a containing apparatus having a container having an opened end and a thread region near the opened end, the above-described closure, and one of a sample collection device and an applicator. The closure is selectively connectable to the opened end of the container in a first configuration and in a second configuration. The connector is disposed in the second portion of the closure body. The one of the sample collection device and the applicator is connected to the connector and extends from the second portion of the closure body away from the first portion of the closure body. When the closure is connected to the opened end of the container in the first configuration, the first thread region of the closure engages the thread region of the container, and the one of the sample collection device and the applicator is disposed outside the container and extends away therefrom. When the closure is connected to the opened end of the container in the second configuration, the second thread region of the closure engages the thread region of the container, and the one of the sample collection device and the applicator is disposed inside the container.

In yet another aspect, the invention provides a closure for a container. The container has an opened end. The closure has a first closure body and a second closure body. The first closure body has a first cylindrical wall and a first top connected to an end of the first cylindrical wall. The second closure body has a second cylindrical wall and a second top connected to an end of the second cylindrical wall. The closure also has a connector disposed in at least one of the first and second closure bodies. The connector is adapted to connect one of a sample collection device and an applicator to the closure. The first top is connected to the second top such that the first and second closure bodies are generally coaxial.

In a further aspect, the first closure body has a first thread region extending inwardly from the first cylindrical wall. The first thread region is complementary to a thread region of the container located near the opened end of the container for engagement therewith. The second closure body has a second thread region extending inwardly from the second cylindrical wall. The second thread region is complementary to the thread region of the container for engagement therewith.

In another aspect, the invention provides a containing apparatus having a container having an opened end and a thread region near the opened end, the above-described closure, and one of a sample collection device and an applicator. The closure is selectively connectable to the opened end of the container in a first configuration and in a second configuration. The connector is disposed in the second closure body. The one of the sample collection device and the applicator is connected to the connector and extends from the second closure body away from the first closure body. When the closure is connected to the opened end of the container in the first configuration, the first thread region of the first closure body engages the thread region of the container, and the one of the sample collection device and the container is disposed outside the container and extends away therefrom. When the closure is connected to the opened end of the container in the second configuration, the second thread region of the second closure body engages the thread region of the container, and the one of the sample collection device and the applicator is disposed inside the container.

In another aspect, the invention provides a containing apparatus having one of the above-mentioned closures, a first container having a thread region engaging the first thread region of the closure, and a second container having a thread region engaging the second thread region of the closure.

In yet another aspect, the invention provides a method of collecting a sample using a containing apparatus. The containing apparatus includes a container, a closure having a first portion and a second portion opposite the first portion, and a sample collection device connected to the closure. The sample collection device extends from the second portion of the closure away from the first portion of the closure. The method comprises: applying the sample collection device to the sample to be collected by holding the container, the container having the first portion of the closure screwed on an opened end thereof; unscrewing the first portion of the closure from the opened end of the container; inserting the sample collection device in the container; and screwing the second portion of the closure to the opened end of the container.

In yet another aspect, the invention provides a closure for a container. The container has an opened end. The closure has a closure body. The closure body has a first cylindrical portion and a second cylindrical portion opposite the first portion. One of a sample collection device and an applicator is connected to the closure body and extends from the second cylindrical portion of the closure body away from the first portion of the closure body.

Embodiments of the present invention each have at least one of the above-mentioned objects and/or aspects, but do not necessarily have all of them. It should be understood that some aspects of the present invention that have resulted from attempting to attain the above-mentioned objects may not satisfy these objects and/or may satisfy other objects not specifically recited herein.

Additional and/or alternative features, aspects, and advantages of embodiments of the present invention will become apparent from the following description, the accompanying drawings, and the appended claims.

BRIEF DESCRIPTION OF THE DRAWINGS

For a better understanding of the present invention, as well as other aspects and further features thereof, reference is made to the following description which is to be used in conjunction with the accompanying drawings, where:

FIG. 12A is a cross-section of another alternative embodiment of the closure of FIG. 1 having two closure bodies, with the two closure bodies shown prior to assembly;

FIG. 12B is cross-section of the closure of FIG. 12A with the two closure bodies connected to each other;

FIG. 14 is a cross-section of another alternative embodiment of a containing apparatus;

FIG. 15 is a cross-section of an alternative embodiment of a closure for use with the containing apparatus of FIG. 14;

FIG. 16 is a cross-section of another alternative embodiment of a closure for use with the containing apparatus of FIG. 14;

FIG. 17 is a side elevation view of an alternative embodiment of a containing apparatus;

DETAILED DESCRIPTION OF THE PREFERRED EMBODIMENTS

Figure 1:
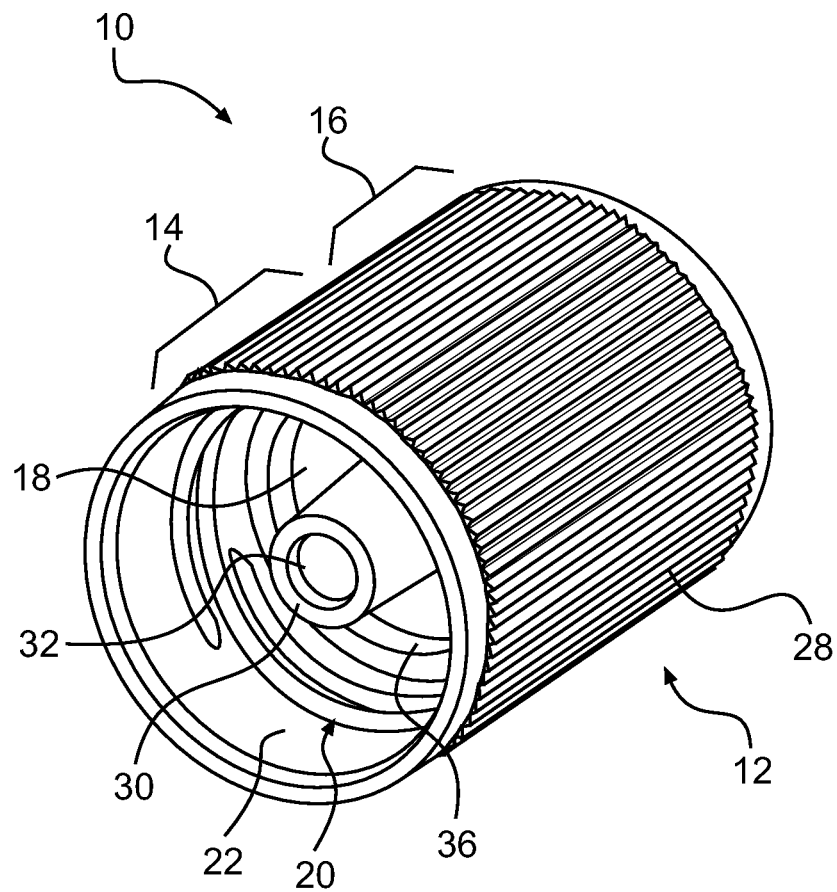
FIG. 1 is a perspective view of a closure for a container.
Figure 2:
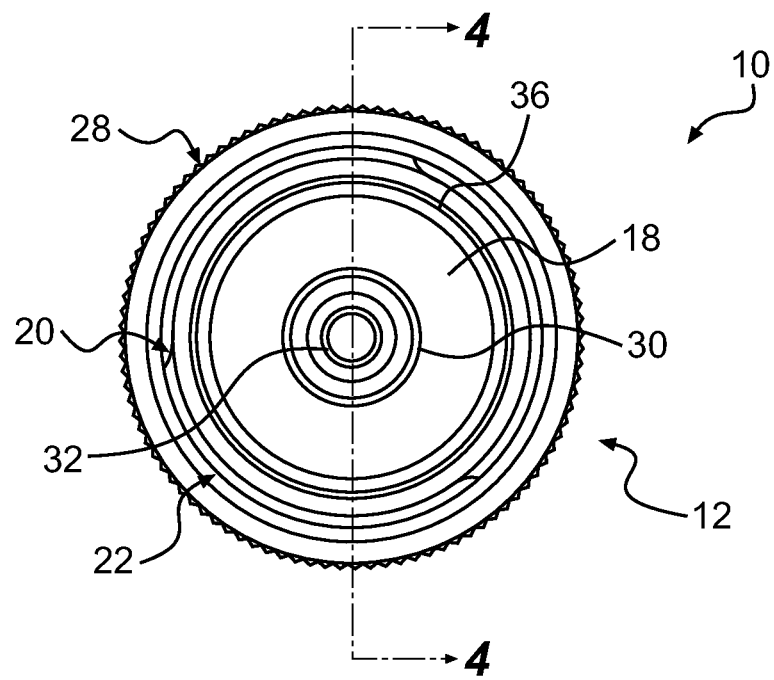
FIG. 2 is an end view of the closure of FIG. 1.
Figure 3:
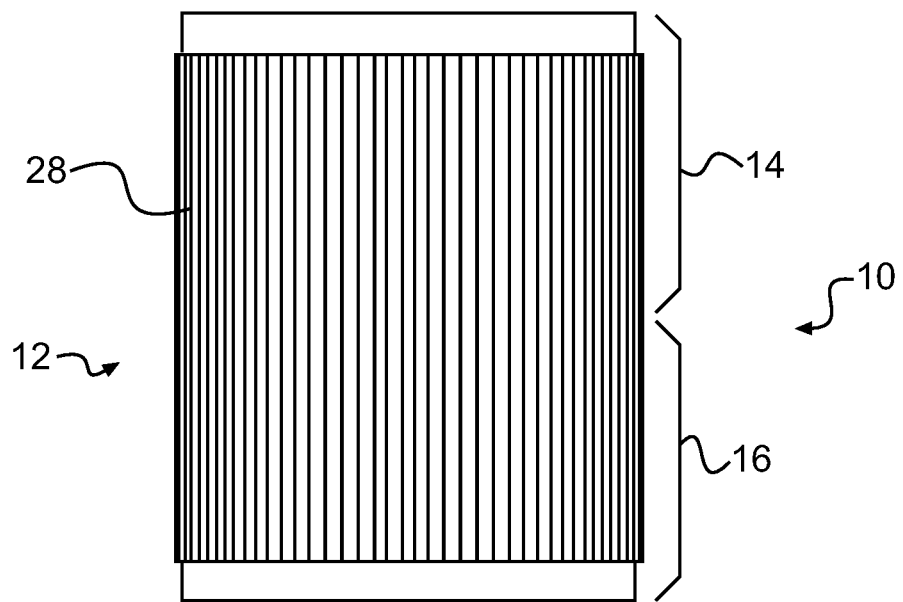
FIG. 3 is a side elevation view of the closure of FIG. 1.

A closure 10 for a container in accordance with aspects of the present invention will be described with respect to FIGS. 1 to 4. As should be understood from FIGS. 1 to 4, the closure 10 is intended for use with a container having a thread region on an outer surface thereof. The closure 10 has a closure body 12 separated in two cylindrical portions 14 and 16 by a closure wall 18. The cylindrical portion 14 is provided with a thread region 20 extending inwardly from a cylindrical interior wall 22 thereof. Similarly, the cylindrical portion 16 is provided with a thread region 24 extending inwardly from a cylindrical interior wall 26 thereof. Both thread regions 20 and 24 are designed to complement a thread region of the container to which the closure 10 is to be connected, thus allowing both portions 14 and 16 to be screwed onto the container. Although each thread region 20, 24 is shown as having a single thread, it is contemplated that each thread region 20, 24 could have multiple threads should this be required to complement the thread region of the container to which the closure 10 is to be connected. An exterior surface 28 of the closure body 12 is ridged in order to facilitate handling of the closure 10 such as when screwing or unscrewing the closure 10 onto or from the container. Although the closure body 12 is shown as having a generally cylindrical outer shape, it is contemplated that it could have other shapes. For example, the outer shape of the closure body 12 could be polygonal in order to prevent the closure from rolling on a surface when it is set on its side.

Figure 4:
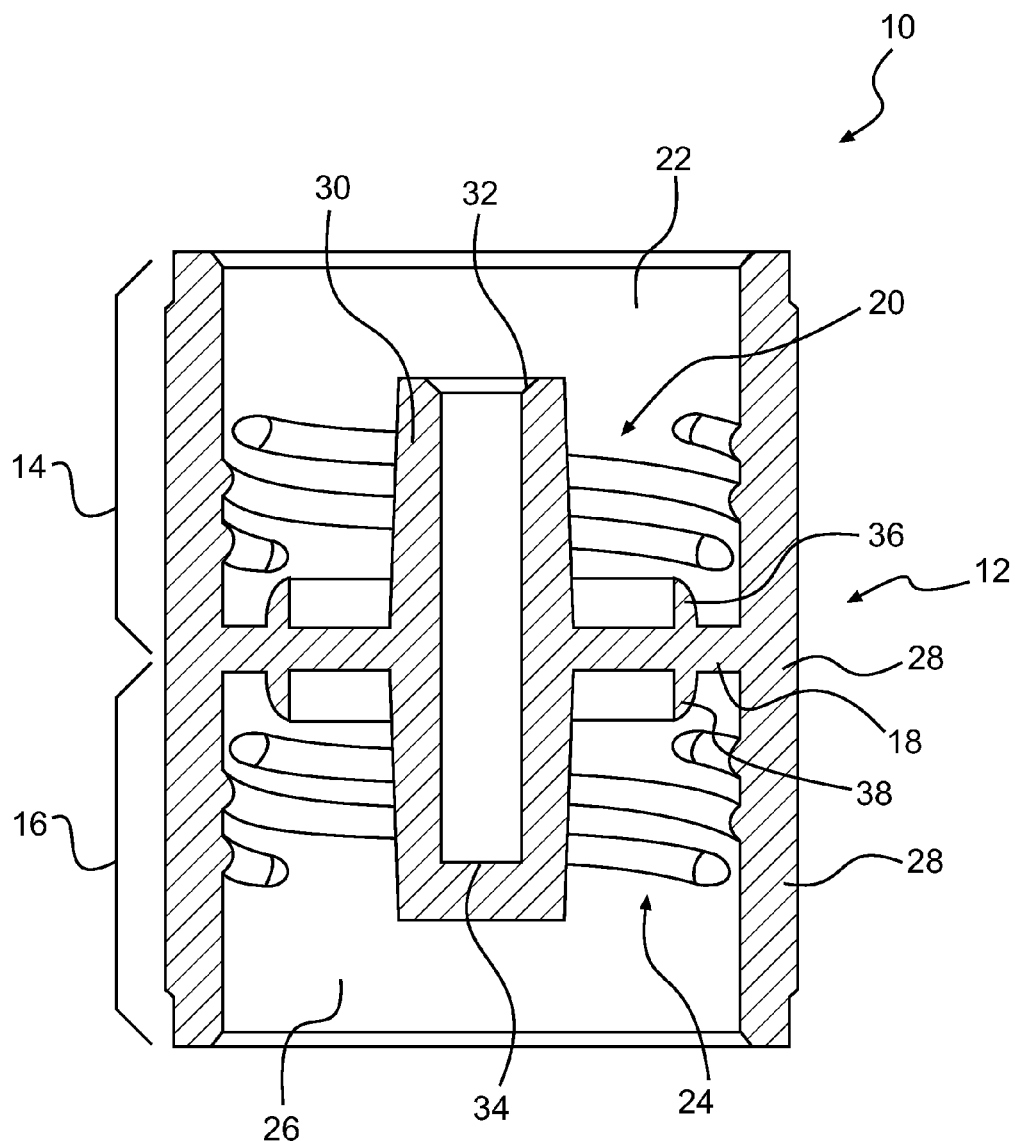
FIG. 4 is a cross-section of the closure of FIG. 1 taken through line A-A of FIG. 2.

The closure 10 has a connector 30 which extends from and through the closure wall 18 in the spaces defined by the cylindrical interior walls 22, 26 of portions 14, 16. The connector 30 has a hollow generally cylindrical body with an opened end 32 and a closed end 34. As will be discussed in greater detail below, the connector 30 is adapted to connect one of a sample collection device and an applicator. As such, it is contemplated that the connector 30 could have a shape other than generally cylindrical so as to be adapted to receive the particular shape of the sample collection device or applicator. For example, in the case where the sample collection device to be connected has a shaft having a square cross-section, the connector 30 would have a hollow body having a square cross-section. By extending through the closure wall 18 into the portion 16, the connector 30 allows for the hollow cylindrical body to have a substantial length which improves the stability of the sample connection device or applicator received therein. As best seen in FIG. 4, the hollow generally cylindrical body of the connector 30 tapers from the opened end 32 to the closed end 34. The tapering of the hollow generally cylindrical body facilitates the removal of the closure 10 from a mold, in the case where the closure 10 is made using a molding process. The tapering of the hollow generally cylindrical body also allows for reduced manufacturing tolerances and different sizes of a connected portion of the sample collection device or of the applicator to be inserted therein as the hollow generally cylindrical body will accommodate variations in a diameter of the connected portion.

The closure 10 is also provided with a pair of wiper seals 36, 38. As best seen if FIG. 4, the wiper seal 36 extends from the closure wall 18 in the space defined by the cylindrical interior walls 22. Similarly, the wiper seal 38 extends from the closure wall 18 in the space defined by the cylindrical interior walls 26. Both wiper seals 36, 38 are disposed between the connector 30 and their corresponding cylindrical interior wall 22 or 26 in a radial direction of the closure body 12. The opened end of the container is received in the space between the wiper seal 36 and the cylindrical interior wall 22 when the first cylindrical portion 14 is connected to the container and is received in the space between the wiper seal 38 and the cylindrical interior wall 26 when the second cylindrical portion 16 is connected to the container such that the wiper seal 36 or 38, as the case may be, contacts the interior surface of the container to form a fluid-tight seal between the container and the closure 10. It is contemplated that other types of seals could be used.

Preferably, container and the closure 10 should be manufactured such that the fluid-tight seals formed between the container and the closure 10 remain fluid-tight over a wide range of temperatures and atmospheric pressures which can result from long-term storage and transportation of the containing apparatus having the container and the closure, such as during air transport. It is contemplated that one or more of the closure wall 18, the thread regions 20, 24, and the wiper seals 36, 38 could be inlaid with an elastomeric material to improve the seals formed between the container and the closure 10. The elastomeric material could be a thermoplastic elastomer (TPE) inlaid in the closure 10 while the closure 10 is being molded by using a dual-injection molding process.

In the embodiment shown in FIGS. 1 to 4, the closure body 12, the closure wall 18, the thread regions 20, 24, the connector 30, and the wiper seals 36, 38 are all integrally formed. However, it is contemplated that one or more of these elements could be manufactured separately and then connected to the other elements. The closure 10 shown in FIGS. 1 to 4 is injection molded, however other manufacturing methods, such as machining, are contemplated. It is also contemplated that additional features could be added to the closure 10. For example, fillets could be added at one or both of the junctions between the cylindrical portions 14 and 16 and the closure wall 18 to help prevent flaring of the cylindrical portions 14 and 16 and/or the container.

One of the contemplated uses of the closure 10 is as a closure in a containing apparatus to be used to collect samples of biological fluids or tissues for genotyping or disease detection. As such, the material used to make the closure 10 for this type of application should not react with the collected sample and the preserving reagents or transport/stabilizing mediums used in the containing apparatus, nor should any chemicals leach out of or degass from the material into the sample, reagents or mediums. Generally, food and medical grade plastics meet these requirements. The material should also withstand sterilization using irradiation (gamma and electron beam sterilization), autoclaving, ethylene oxide, and inactivation procedures (to kill infectious agents). Furthermore, the material should also withstand long-term storage, low temperatures since samples are often stored or banked at 4° C. or in −20° C. to −80° C. freezers and liquid nitrogen, and high temperatures as some processing or extraction protocols may require incubation at temperatures in the range of 50° C. to 100° C. for example. Finally, the material should be strong enough to not be damaged during transportation, and be able to withstand the extreme temperatures and reduced atmospheric pressure associated with air transport. Some of the materials suitable for this type of application are polypropylene, low-density polyethylene (LDPE), medium-density polyethylene (MDPE), high-density polyethylene (HDPE), polyethylene, polyvinyl chloride (PVC), polycarbonate, and thermoplastic elastomeric materials.

Figure 5A:
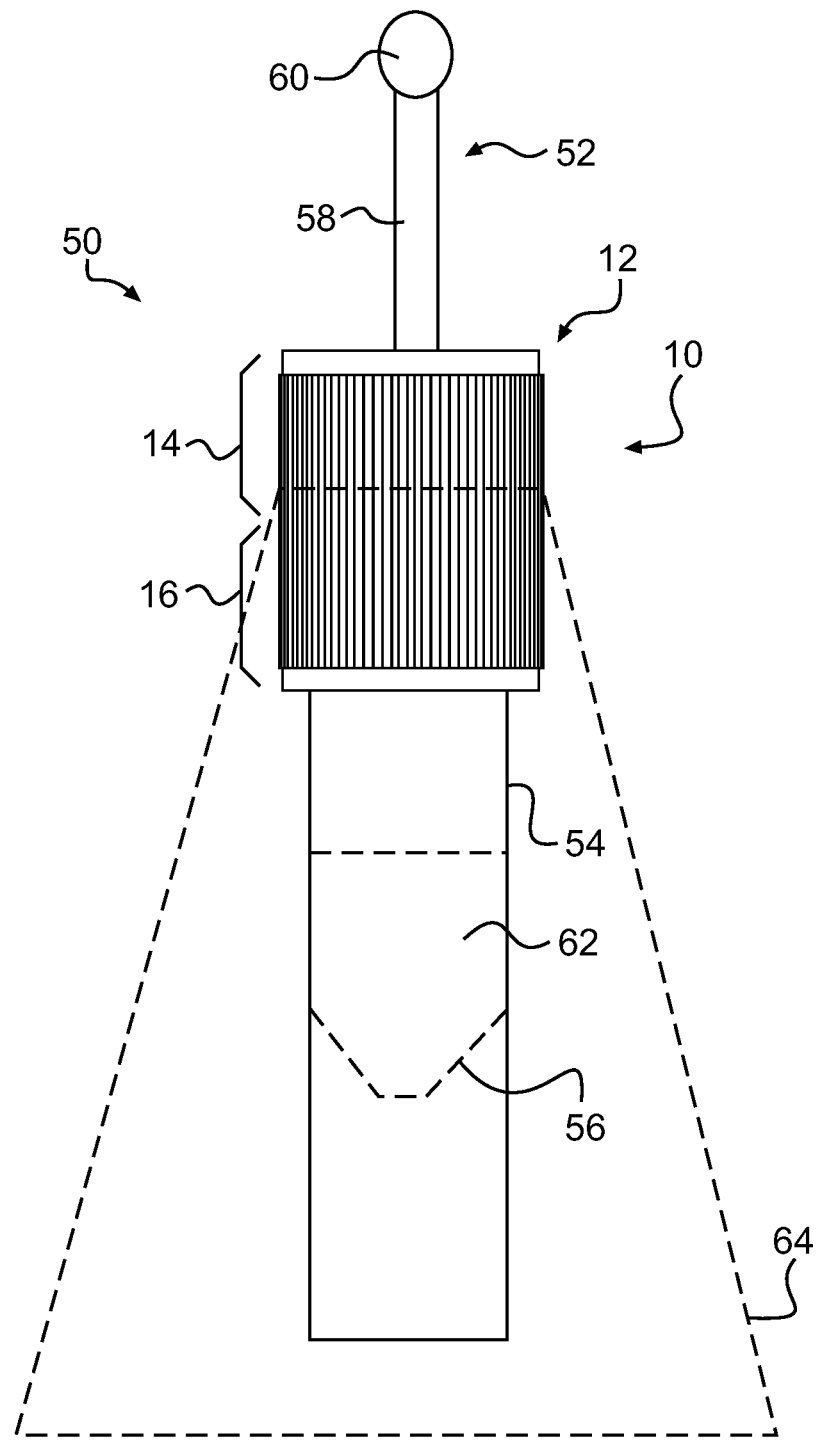
FIG. 5A is a side elevation view of a containing apparatus using the closure of FIG. 1 with one portion of the closure screwed on a container.
Figure 5B:
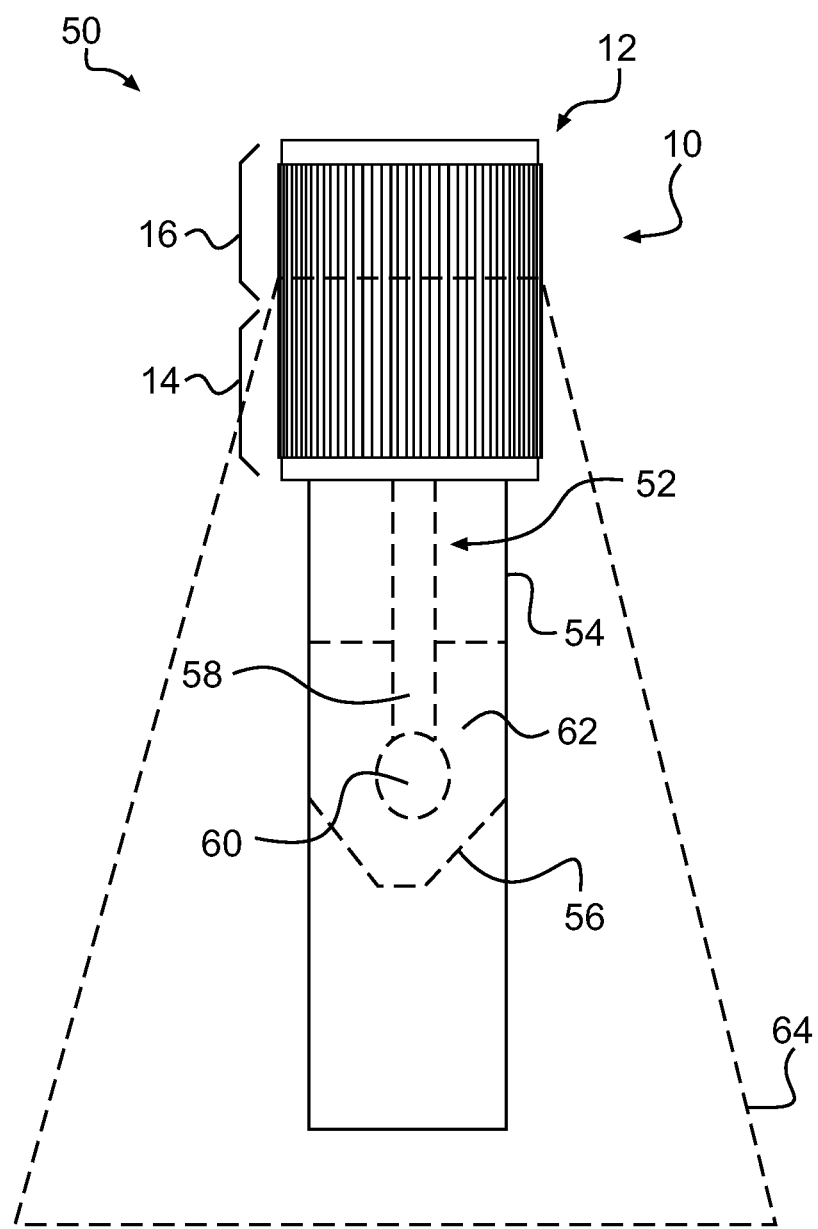
FIG. 5B is a side elevation view of the a containing apparatus of FIG. 5A with another portion of the closure screwed on the container.

Turning now to FIGS. 5A and 5B, a containing apparatus 50 and a method of using the containing apparatus 50 will be described. The containing apparatus 50 includes the closure 10 described above, a container, and a sample collection device 52.

The container is a tube 54 having an opened end and a thread region near the opened end (not shown). The tube 54 has a false bottom 56. This type of tube is advantageous in applications where the containing apparatus 50 is used to collect samples of biological fluids and tissues for genotyping or disease detection as the false bottom 56 makes it easier to reach the sample with a pipette or an automated liquid handler without touching the sides of the tube 54, while the length of the tube 54 makes it suitable for use with standard lab racks and liquid handlers and also makes it easier for users to handle. In an exemplary embodiment, the tube 54 is a 5 ml false-bottom vial made by Starplex Scientific Inc. It is contemplated that other types of containers could be used such as full length vials or bottles. As would be understood, the dimensions of the closure 10 and the characteristics of the thread regions 20, 24 would be adapted to complement the type of container selected and its' thread region.

The sample collection device 52 includes a shaft 58 and a sample collection implement 60. The shaft 58 has one end received in the hollow generally cylindrical connector body of the connector 30, thus connecting the sample collection device 52 to the closure 10 via a friction fit. The sample collection implement 60 is connected to the other end of the shaft 58. In the embodiment shown, the sample collection implement 60 is a swab. It is contemplated that the sample collection implement 60 could be of another type, so as to be suitable for the type of sample to be collected. Examples of other sample collection implements 60 include a sponge, a brush, a spatula, a loop, a scraper, a spoon, a scoop, a depressor, a capillary tube, a tissue punch, an absorbent solid matrix, such as an absorbent paper-like material, and a large bore needle. It is also contemplated that the sample collection device 52 could include a single part, as would be the case where the sample collection device 52 is a tongue depressor for example. It is also contemplated that the sample collection device 52 and the closure 10 could be integrally formed.

The containing apparatus 50 is preferably packaged in a flexible blister sealed to a peal-away backing, but other types of packaging are contemplated. The containing apparatus 50 is preferably packaged assembled as shown in FIG. 5A (i.e. with the portion 16 screwed to the tube 54, and the sample collection device 52 connected to the connector 30), so as to reduce the amount of handling of the sample collection device 52 by a user of the containing apparatus, thus reducing the risk of contamination of the sample. However, it is contemplated that the sample collection device 52 could be disposed in the package disconnected from the rest of the containing apparatus 50, thus allowing for a shorter package. It is also contemplated that the sample collection device 52 could be provided separately from the preassembled closure 10 and tube 54.

In many applications, the sample, once collected, needs to be immersed in a substance, such as a preserving reagent or a transport or stabilizing medium, such as a biomolecule-stabilizing composition, or an assay or processing reagent, such as an extraction reagent, or a reagent having a combination of two or more of these functions. For example, in applications where the sample to be collected is a nucleic acid-containing biological fluid, the substance could be a nucleic acid-stabilizing composition such as those described in International Publication Nos. WO 2003/104251 A2, published Dec. 18, 2003, and WO 2008/040126 A1, published Apr. 10, 2008, the entirety of which are incorporated herein by reference, or a direct to amplification, stabilizing composition such as the one described in International Publication No. WO 2006/096973 A1, published Sep. 21, 2006, the entirety of which is incorporated herein by reference. The containing apparatus 50 includes such a substance, liquid 62, which is placed directly inside the tube 54 prior to packaging. The fluid-tight seal formed by the closure 10 prevents the liquid 62 from leaking out of the tube 54. Alternatively, the liquid 62 could be stored within a breakable membrane, capsule or bladder in the tube 54 that is ruptured when the sample collection device 52 is inserted in the tube 54, as described below (see FIG. 5B), thus releasing the liquid 62 in the tube 54. It is also contemplated that a substance, such as a preserving reagent or a transport or stabilizing medium, or a portion thereof, could be dried onto a surface of the closure 10 (a surface of the closure wall 18 for example) that would face the interior of the container once the sample has been collected. In this embodiment, it is possible that the closure is used without an attached sample collection device or applicator. It is also contemplated that a substance, such as a desiccant, a preserving reagent or a transport or stabilizing medium, could be dried onto the internal surface of the tube 54.

A method of using the containing apparatus 50 to collect a sample will now be described. For simplicity, the method will be described assuming that the liquid 62 is already present in the tube 54 and that the sample collection device 52 is connected to the connector 30. It should be understood that the additional steps of pouring the liquid 62 in the tube 54 and connecting the sample collection device 52 to the connector 30 would be necessary if this was not the case. It is also contemplated that the sample could be collected into an empty tube 54 (i.e. a tube 54 which does not have the liquid 62 therein).

Figure 19C:
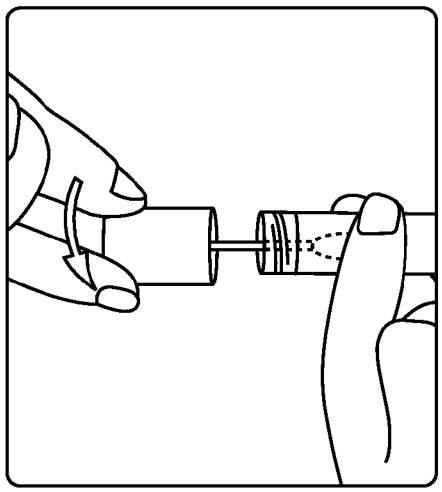
FIGS. 19A to 19C illustrate schematically steps for collecting a nasal sample from cattle using one embodiment of a containing apparatus.
Figure 19B:
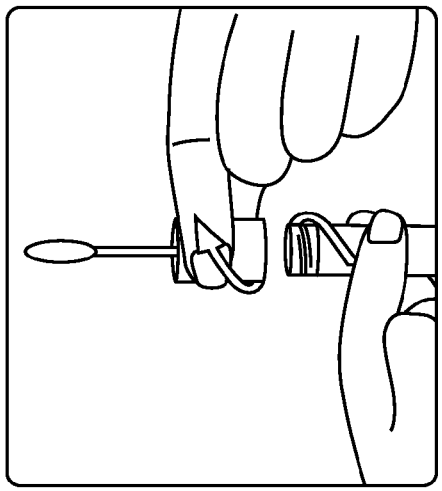
Figure 19A:
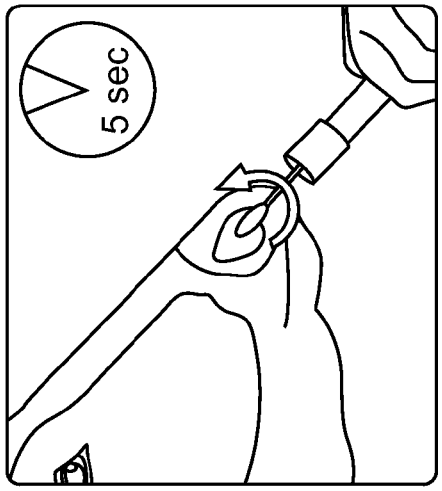

The user of the containing device 50 first removes the containing apparatus 50, which is already in the configuration shown in FIG. 5A, from the packaging. As described above, when the containing apparatus 50 is in the configuration shown in FIG. 5A, the cylindrical portion 16 of the closure 10 is screwed on the opened end of the tube 54 such that the thread region 24 engages the thread region of the tube 54 and the sample collection device 52 extends from the other end of the closure 10. In this configuration, the opened end of the tube 54 abuts the wiper seal 38 and the closure wall 18 thereby forming a fluid-tight seal between the tube 54 and the closure 10. The user then holds the tube 54, which acts as a handle or collection wand, and applies the sample collection implement 60 to the sample to be collected, such as human, bovine, sheep, or canine nasal mucous for example. FIG. 19A shows this step for the collection of a nasal sample from a cattle. As should be understood, the motion necessary to apply the sample collection implement 60 to the sample in order to collect the sample will vary depending on the sample source and the type of sample collection implement 60 being used. For example, a brushing motion would be used when the sample collection implement 60 is a brush, a scraping motion would be used when the sample collection implement 60 is a scraper, and a stabbing motion would be used when the sample collection implement 60 is a needle or tissue punch. The user then unscrews the closure 10 from the tube 54 as shown in FIG. 19B, turns the closure 10 over with the sample collection device 52 connected to the connector 30, and inserts the sample collection device 52 in the tube 54 as shown in FIG. 19C. The user then screws the cylindrical portion 14 of the closure 10 on the opened end of the tube 54 such that the thread region 20 engages the thread region of the tube 54. The containing apparatus 50 is now in the configuration shown in FIG. 5B and is, for example, ready to be sent to the laboratory for testing. In this configuration, the opened end of the tube 54 abuts the wiper seal 36 and the closure wall 18 thereby forming a fluid-tight seal between the tube 54 and the closure 10. As can be seen in FIG. 5B, when the containing apparatus 50 is held upright, the sample collection implement 60 is immersed in the liquid 62.

As should be understood from the above, the method of using the containing apparatus 50 is intuitive and easy to perform even for the untrained user. The method of using the containing apparatus 50 is simple enough that instructions on how to use the apparatus 50 can be provided as pictorial instructions. Also, at least in the embodiment where the containing apparatus 50 comes packaged with the sample collection device 52 connected to the connector 30, the user does not have to touch the sample collection device 52 at any point of the sample collection procedure, thus reducing the likelihood of contamination of the sample.

It is contemplated that once the sample has been collected (i.e. when the containing apparatus 50 is in the configuration shown in FIG. 5B), that a tamper-evident feature could be added to the containing apparatus 50. In the example where the containing apparatus 50 is sent to a laboratory for testing, the tamper-evident feature would allow the laboratory personnel to know if the sample has been tampered with prior to reaching the laboratory. Examples of tamper-evident features that could be used include, but are not limited to, a tape that is attached both to the closure 10 and the tube 54, a seal, a label, and one or more plastic rings that detach from the closure 10 when it is unscrewed from the tube 54. It is also contemplated that the tube 54 could include identification information such as a bar code or identification number to facilitate tracking and identification of the containing apparatus 50.

It is contemplated that a sheath 64 (shown in phantom in FIG. 5A) can be connected to the closure body 10. Although shown as being connected near a center of the closure 10, it is contemplated that the sheath 64 could be connected near an end of the closure 10. Prior to the collection of the sample (i.e. when the containing apparatus 50 is in the configuration shown in FIG. 5A), the sheath 64 is placed so as to cover the hand of the user holding the tube 54, and therefore the tube 54, so as to keep the user's hand clean and protected during the collection of the sample. Once the sample has been collected (i.e. when the containing apparatus 50 is in the configuration shown in FIG. 5B), the sheath 64 is turned over so as to once again cover the tube 54 (as shown in FIG. 5B), such that the surface of the sheath 64 which may have been contaminated during the collection of the sample faces inwardly. It is contemplated that the sheath 64 could then be sealed to enclose the tube 54 therein. Alternatively, the sheath 64 could be removed from the closure body 10 and discarded once the sample collection device 52 has been applied to the sample to be collected or at any time thereafter, such as once the containing apparatus 50 is in the configuration shown in FIG. 5B.

It is contemplated that the containing apparatus 50 could also be used to apply a substance to a surface. For this type of application, the sample collection device 52 would be replaced by an applicator (not shown). The applicator includes a shaft similar to the shaft 58 of the sample collection device 52, and an application implement. The applicator is connected to the connector 30 of the closure 10 in the same manner as the sample collection device 52. It is contemplated that some types of sample collection devices could also be used as applicators.

When the containing apparatus 50 is to be used to apply a substance to a surface, the containing apparatus 50 would be packaged as shown in FIG. 5B (i.e. with the applicator inside the tube 54). The liquid 62 in the tube 54 could be, for example, a medicine that needs to be applied topically. To apply the liquid 62, the user first unscrews the closure 10 from the tube 54, turns the closure 10 over, and then screws the closure 10 back on the tube 54 as shown in FIG. 5A. Then, by using the tube 54 as a handle or collection wand, the user applies the liquid 62 to the required surface. Once the application is completed, the user can discard the containing apparatus 50, or the user can unscrew the closure 10 from the tube 54 and screw the closure 10 back on the tube 54 as shown in FIG. 5B such that the containing apparatus 50 can be used again for further applications of the liquid 62.

Turning now to FIGS. 6 to 18, various alternative embodiments of the closure 10 and of the containing apparatus 50 will be described. For simplicity, elements of these embodiments which are similar to those of the closure 10 and of the containing apparatus 50 have been labelled with the same reference numerals and will not be described again in detail. It should be understood that these alternative embodiments of the closure 10 and of the containing apparatus 50 could be manufactured by methods similar to those described above and could be made of materials similar to those described above.

Figure 6:
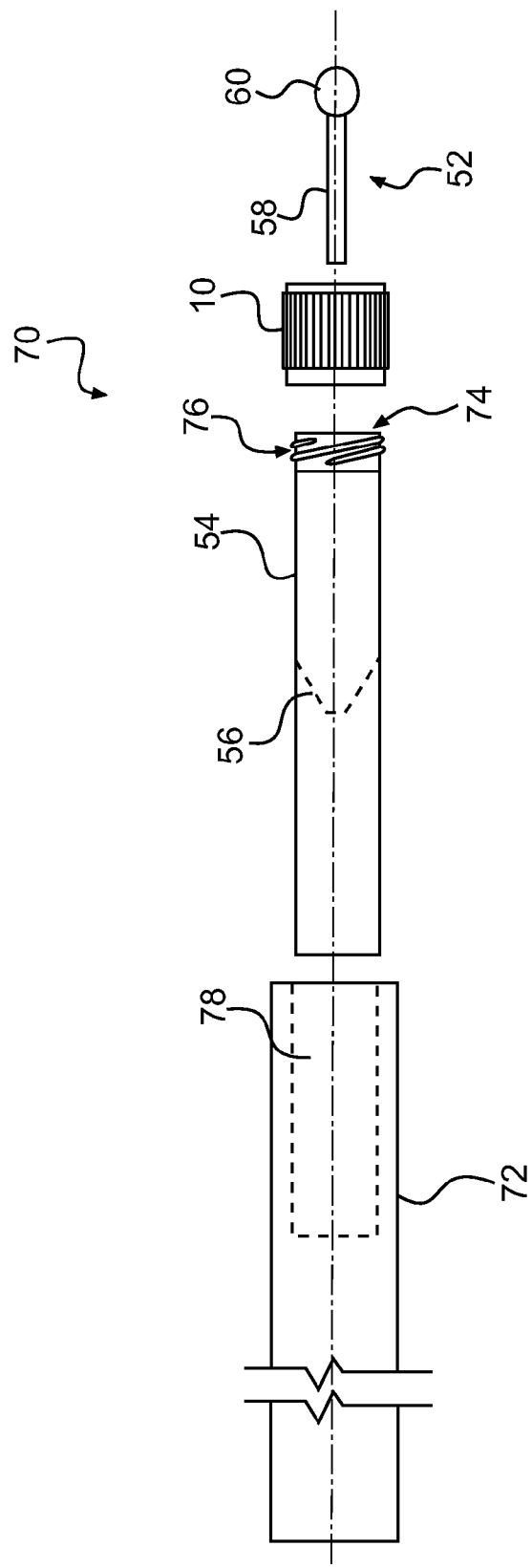
FIG. 6 is an exploded side elevation view of an alternative embodiment of a containing apparatus.

FIG. 6 illustrates an exploded view of a containing apparatus 70. The containing apparatus 70 has the same elements has the containing apparatus 50 with the addition of an extension 72. In FIG. 6, the opened end 74 and the thread region 76 of the tube 54 can be seen. The extension 72 has a recess 78 (shown in phantom) at one end thereof to receive the bottom end of the tube 54, thereby connecting the extension 72 to the tube 54. In this embodiment, the user uses the extension 72 as a handle or collection wand rather than the tube 54 itself, as in the containing apparatus 50. The extension 72 therefore allows the user to collect a sample from a greater distance.

FIGS. 7 to 12B show various embodiments of closures, all of which could be used with the containing apparatuses 50 and 70.

Figure 7:
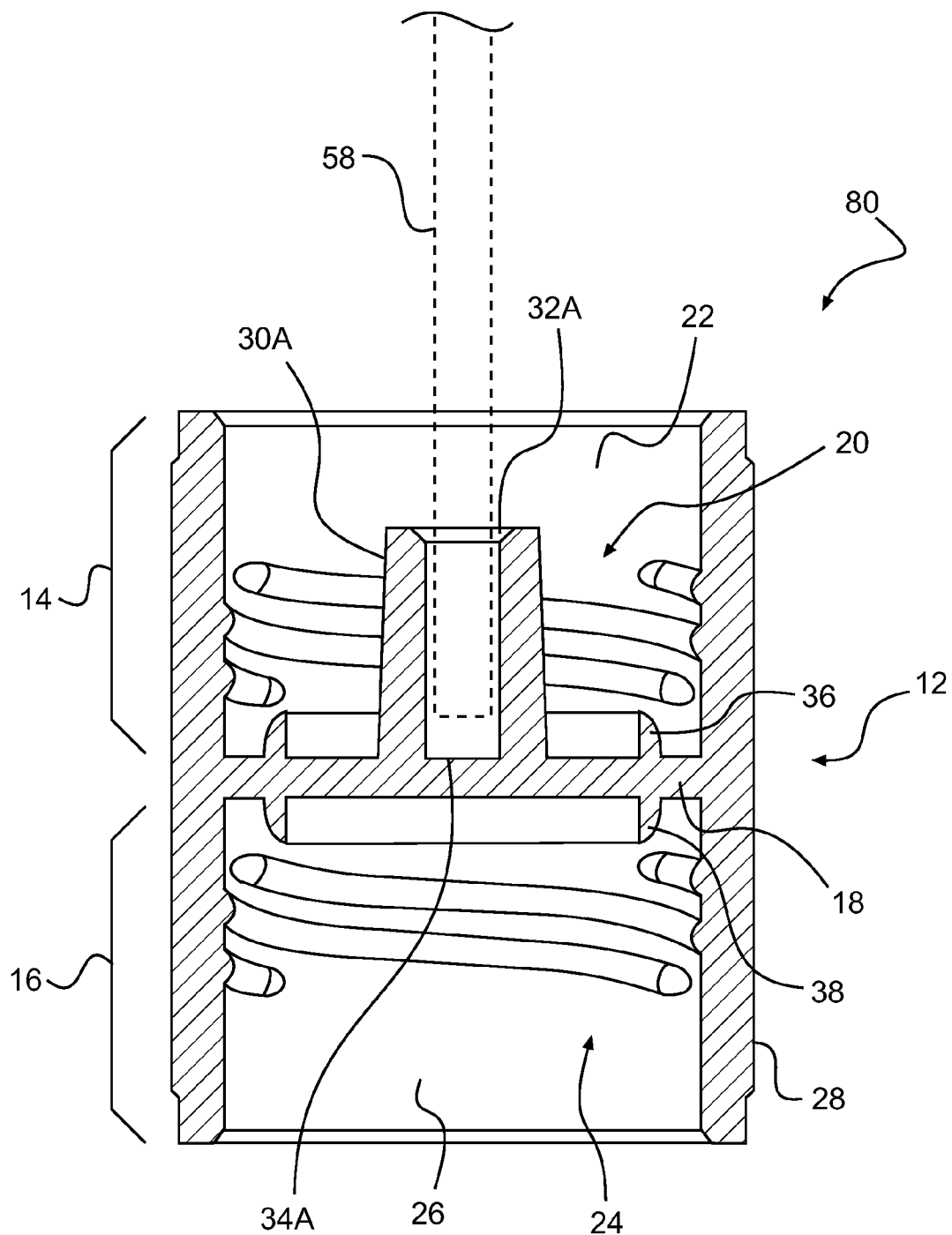
FIGS. 7 to 11 are cross-sections of alternative embodiments of the closure of FIG. 1.

FIG. 7 shows a cross-section of a closure 80. The closure 80 has a connector 30A. The connector 30A has a hollow generally cylindrical connector body having an opened end 32A and a closed end 34A. As can be seen, the connector 30A extends only on one side of the closure wall 18. The closed end 34A corresponds to the outer surface of the closure wall 18. It is contemplated that the closed end 34A could be above or recessed into the closure wall 18. The shaft 58 of the sample collection device 58 connected to the connector 30A is also shown (in phantom) in FIG. 7.

Figure 8:
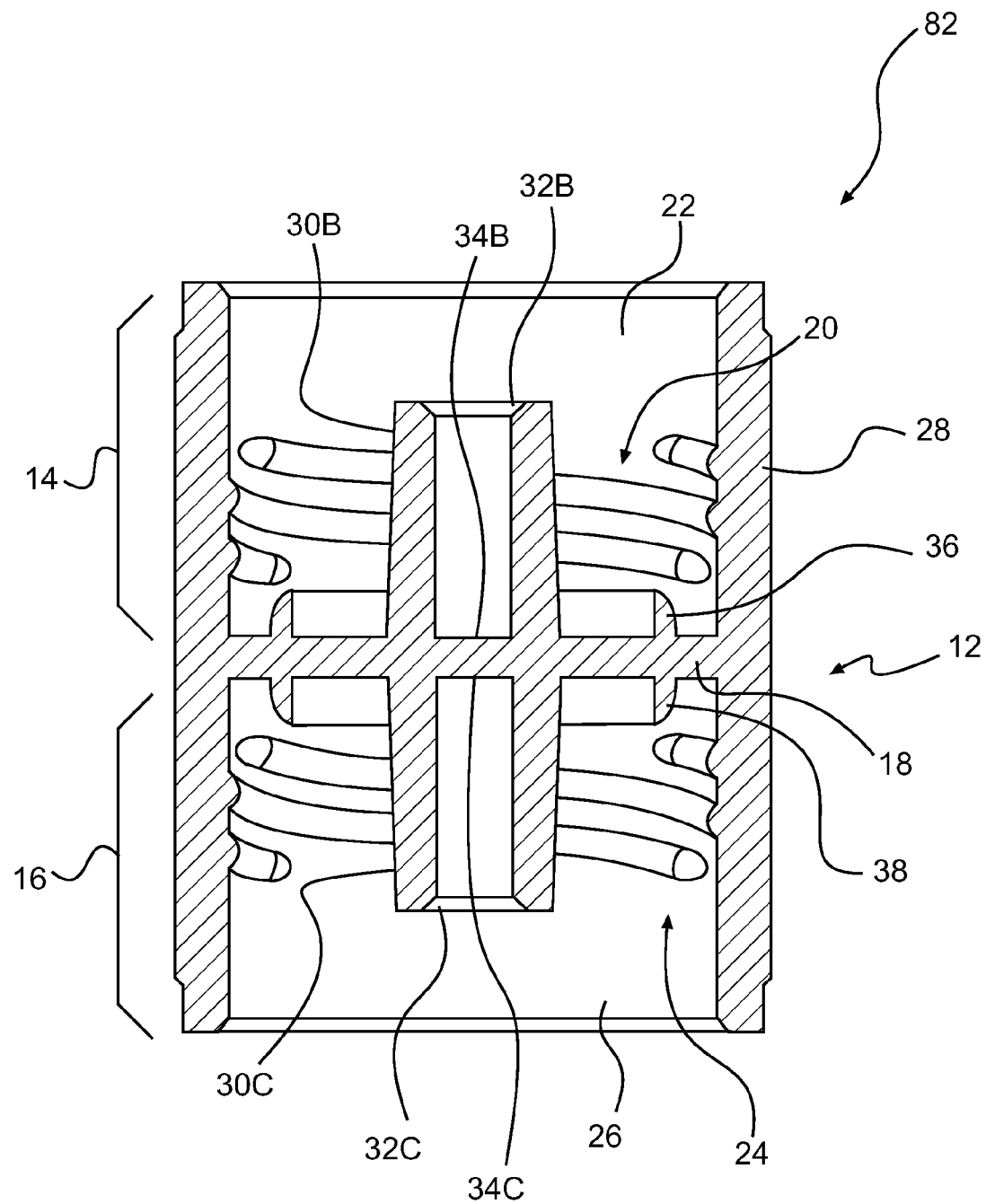

FIG. 8 shows a cross-section of a closure 82. The closure 82 has two connectors 30B and 30C. Each of the connectors 30B and 30C has a hollow generally cylindrical connector body having an opened end 32B or 32C and a closed end 34B or 34C respectively. As can be seen, the connector 30B extends on one side of the closure wall 18 and the connector 30C extends on the other side of the closure wall 18. The closure 82 facilitates the assembly of the containing apparatuses 50 and 70 since the sample collection device can be connected to either side of the closure 82. It is contemplate that sample collection devices could be connected to both sides of the closure 82.

Figure 9:
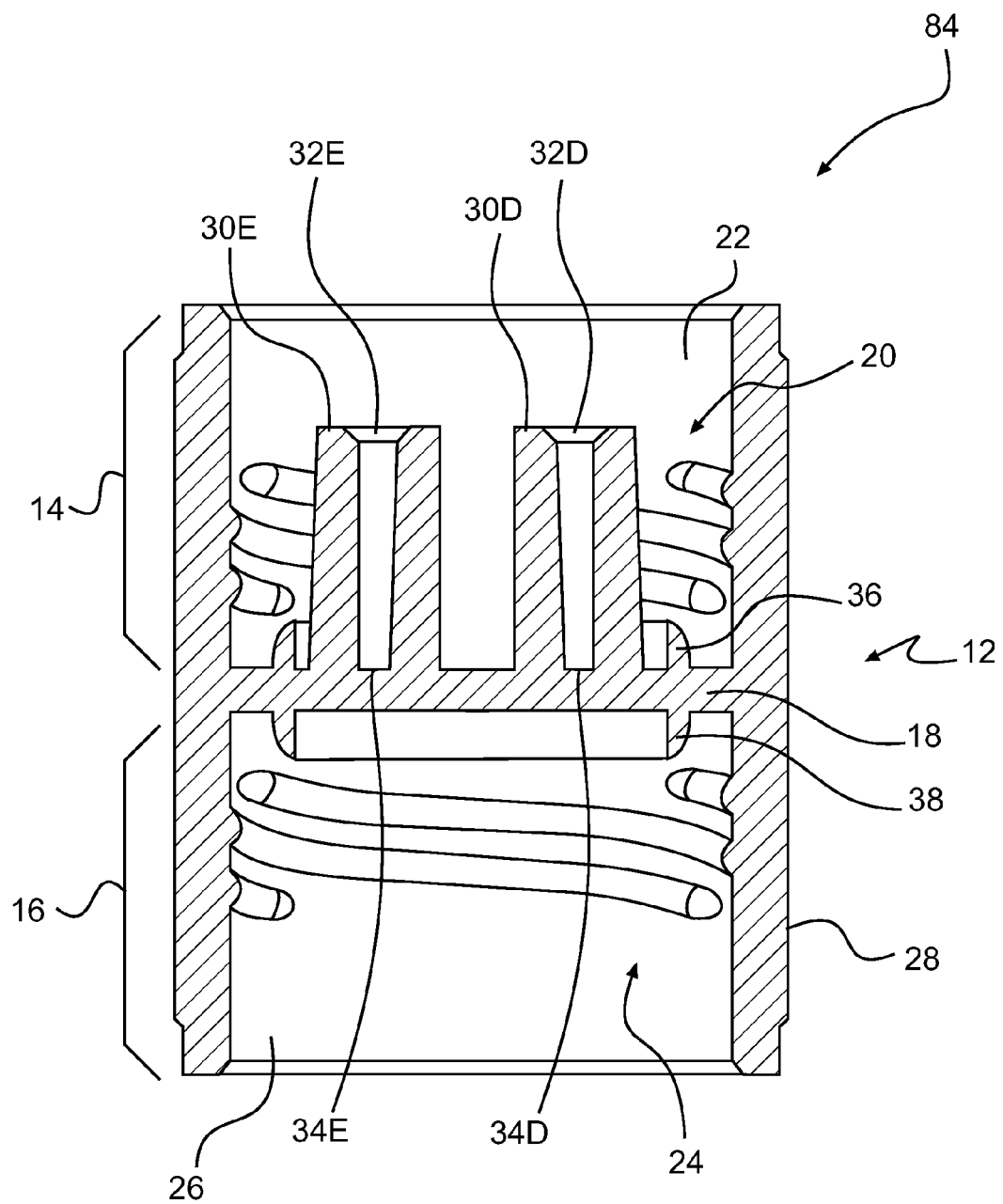

FIG. 9 shows a cross-section of a closure 84. The closure 84 has two connectors 30D and 30E. Each of the connectors 30D and 30E has a hollow generally cylindrical connector body having an opened end 32D or 32E and a closed end 34D or 34E respectively. As can be seen, both of the connectors 30D and 30E extend on the same side of the closure wall 18 and are disposed side by side radially inwardly of the wiper seal 36. The closure 84 allows two sample collection devices 52, or two applicators, or one of each, to be connected to the closure 84.

Figure 10:
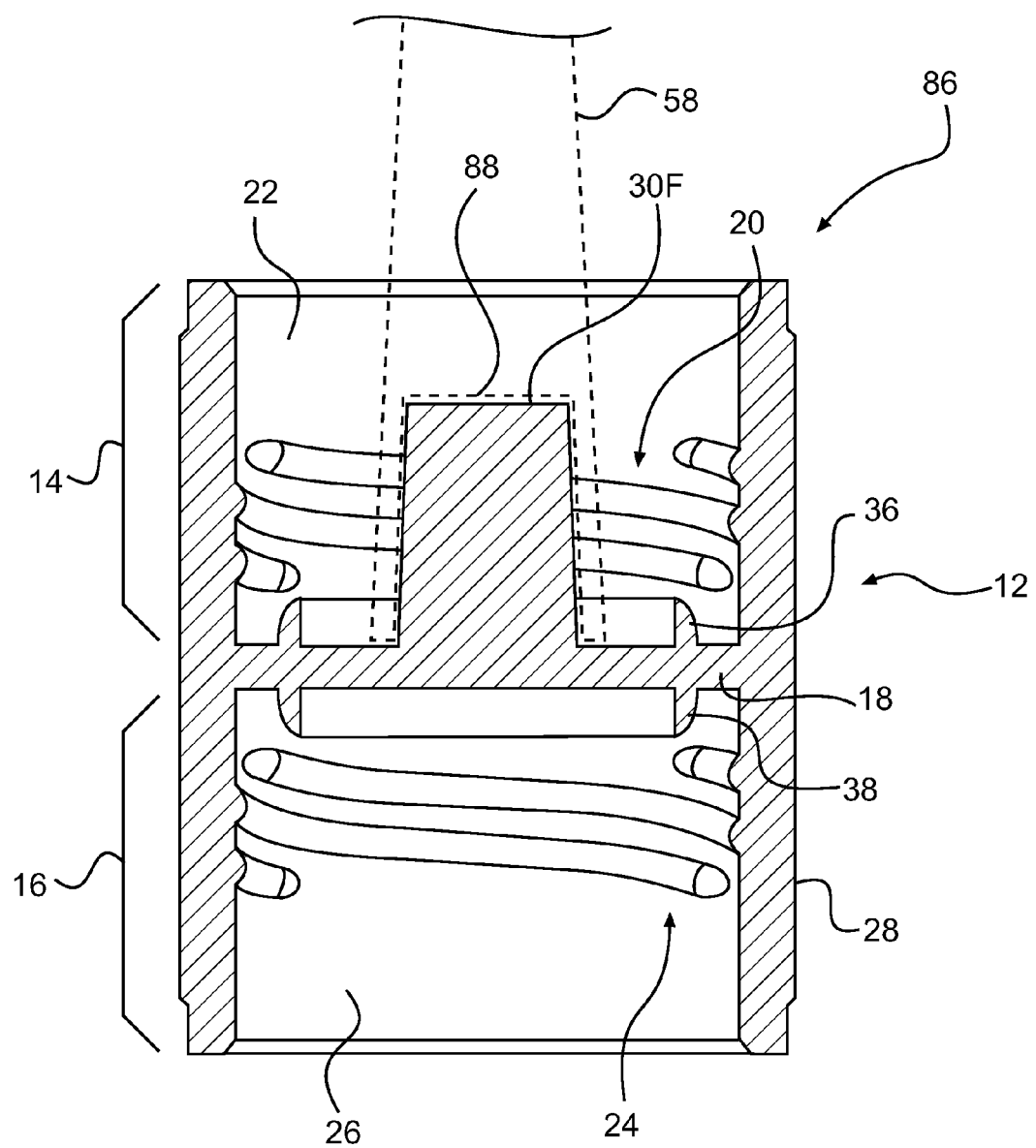

FIG. 10 shows a cross-section of a closure 86. The closure 86 has a connector 30F. The connector 30F has a solid generally cylindrical connector body. In order to connect the sample collection device 52 to the connector 30F, the shaft 58 of the sample collection device 52 has a recess 88 inside which the connector 30F can be received.

Figure 11:
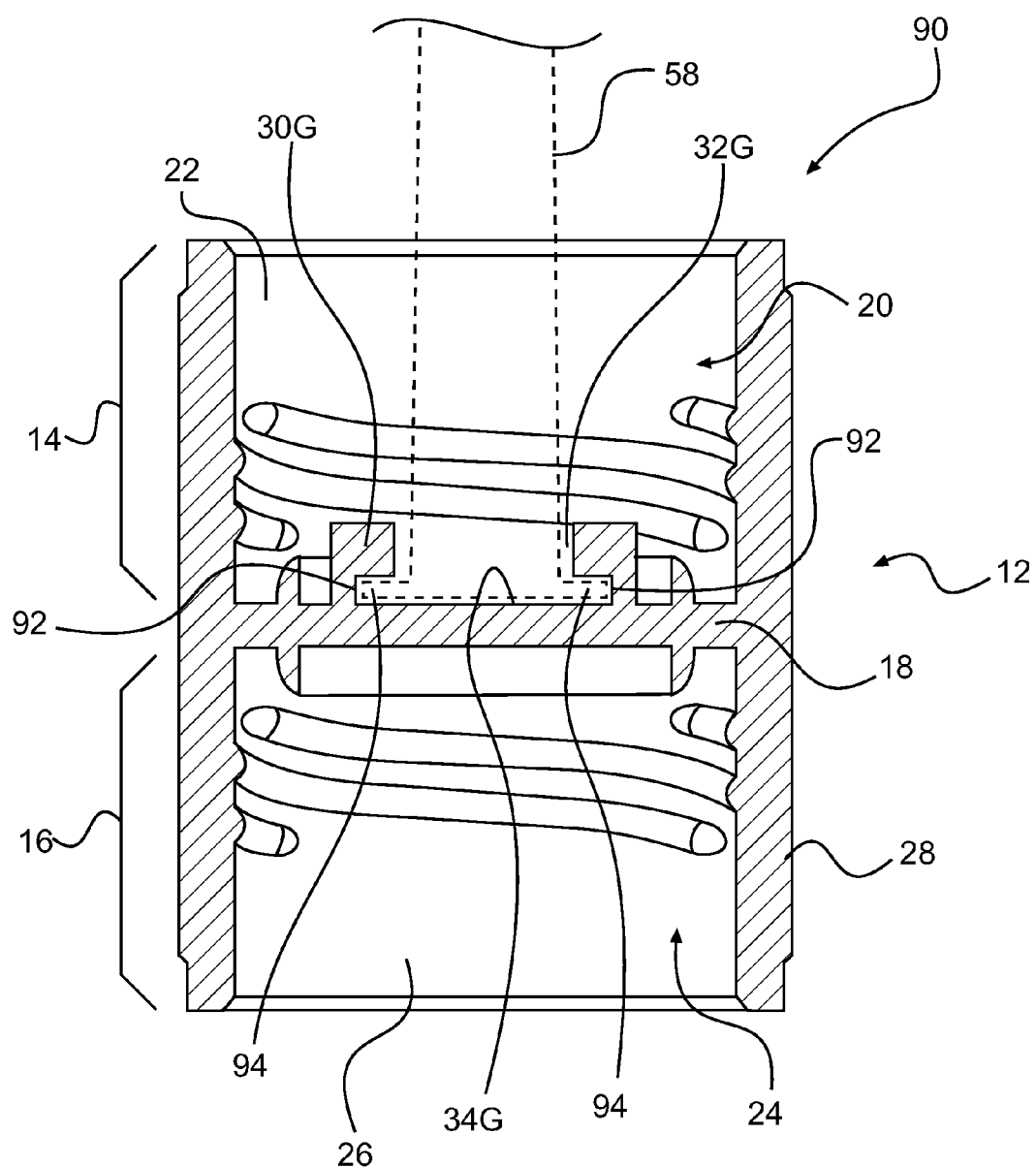
Figure 13A:
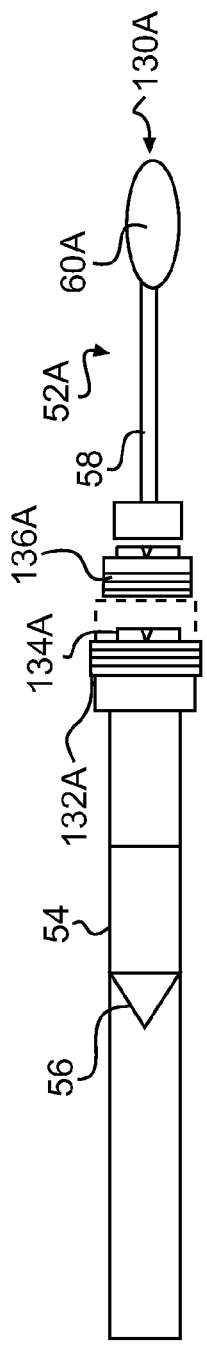
FIGS. 13A to 13D are schematic side elevation views of alternative embodiments of a containing apparatus.
Figure 13B:
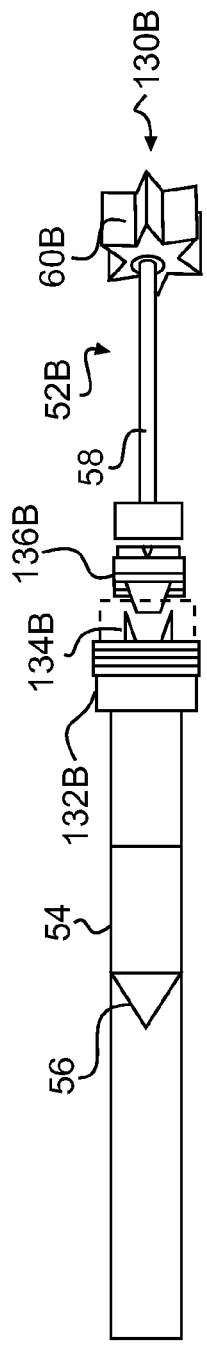
Figure 13C:
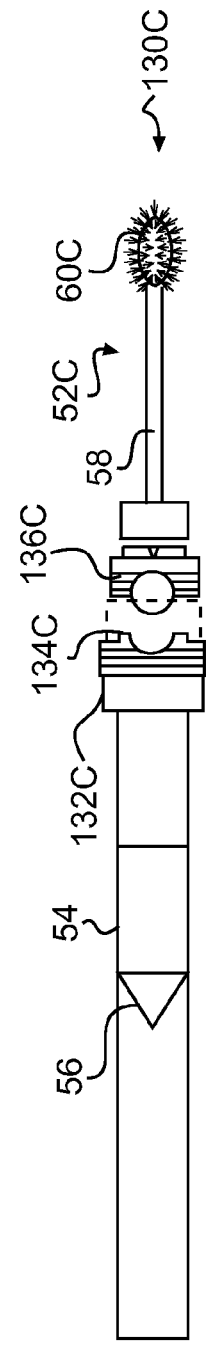
Figure 13D:
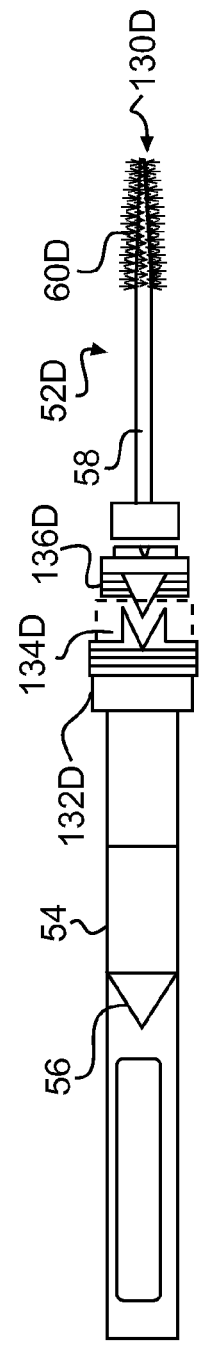

FIG. 11 shows a cross-section of a closure 90. The closure 90 has a connector 30G. The connector 30G has a hollow generally cylindrical connector body having an opened end 32G and a closed end 34G. The connector 30G also has one or more recesses 92 formed in an interior wall of the connector 30G. In order to connect the sample collection device 52 to the connector 30G, the shaft 58 of the sample collection device 52 has one or more tabs 94. When the shaft 58 is inserted inside the connector 30G, the one or more tabs 94 initially bend and then straighten out once they reach the one or more recesses 92, thereby retaining the shaft 58 in the connector 30G.

FIG. 12B shows a cross-section of a closure 100. The closure 100 is made of two closure bodies 102, 104 which are connected to each other. FIG. 12A shows a cross-section of the two closure bodies 102, 104 before they are connected to each other. The closure body 102 has a cylindrical wall 106 and a top 108 connected to an end of the cylindrical wall 106. A thread region 110 extends inwardly from the cylindrical wall 106. A connector 112 similar to the connector 30A of the closure 80 extends from the top 108. A wiper seal 114 having a circular cross-section extends from the top 108 and is disposed between the connector 112 and the cylindrical wall 106 in a radial direction of the closure body 102. An exterior surface 116 of the closure body 102 is ridged in order to facilitate handling of the closure 100. The closure body 104 has a cylindrical wall 118 and a top 120 connected to an end of the cylindrical wall 118. A thread region 122 extends inwardly from the cylindrical wall 118. A wiper seal 124 having a circular cross-section extends from the top 108. An exterior surface 126 of the closure body 104 is ridged in order to facilitate handling of the closure 100. Both thread regions 110 and 122 are designed to complement a thread region of the container to which the closure 100 is to be connected. To form the closure 100, the top 108 is connected to the top 120 such that both closure bodies 102, 104 are generally coaxial as shown in FIG. 12B. It is contemplated that the top 108 could be connected to the top 120 by welding, such as by friction welding. It is also contemplated that the top 108 could be connected to the top 120 by bonding, such as by a liquid adhesive or a double-sided tape adhesive. It is also contemplated that the top 108 could be connected to the top 120 by mechanical fastening, such as by providing the male part of a fastener on one of the tops 108 and 120 and the female part of a fastener to the other one of the tops 108 and 120. Another contemplated method of mechanically fastening the closure bodies 102 and 104 to each other consists in heat shrinking a plastic tubing around the two closure bodies 102 and 104 arranged with their tops 108 and 120 abutting each other. It is also contemplated that adhesive could be applied to the inner surface of the tubing to strengthen the connection. It is also contemplated that the closure body 104 could be identical to the closure body 102, such that the closure 100 resembles the closure 82 described above. It is also contemplated that one or both of the closure bodies 102, 104 could be modified such that the closure 100 resembles any one of closures 84, 86 and 90.

FIGS. 13A to 13D illustrate containing apparatuses 130A to 130D respectively. Containing apparatuses 130A to 130D include closures 132A to 132D (with a portion thereof shown in phantom to show internal features of thereof) having a construction similar to the construction of closure 10 described above, but with a different type of connector. The closures 132A to 132D have each have a male or female connector 134A to 134D, respectively, adapted to connect a corresponding female or male connector of a corresponding adaptor 136A to 136D, respectively. The adaptors 136A to 136D are used to connect the sample collection devices 52A to 52D respectively. As can be seen, each of the closures 132A to 132D uses a different geometry of male or female connector 134A, 134B, 134C, or 134D to connect their corresponding adaptor 136A, 136B, 136C, or 136D. FIGS. 13A to 13D also show different types of sample collection devices 52A to 52D. The sample collection implement 60A of sample collection device 52A is a swab. The sample collection implement 60B of sample collection device 52B is a sponge shaped to increase its surface area. The sample collection implement 60C of sample collection device 52C is a brush. The sample collection implement 60C of sample collection device 52C is a conical brush. It is contemplated that different sample collection devices could have identical adaptors, such that different sample collection devices could be provided on a closure.

It is contemplated that the closure bodies 102 and 104 of the closure 100 described above could be provided with male/female connectors similar to those described above with respect to FIGS. 13A to 13D to connect the closure body 102 to the closure body 104.

Turning now to FIG. 14, a containing apparatus 140 will be described. The containing apparatus 140 includes the sample collection device 52 described above, a tube 142, a closure 144, and a liquid 62 in the tube 142. The tube 142 has an opened end 146 and a thread region 148. As can be seen, the thread region 148 is disposed internally of the opened end 146; therefore, the thread regions of the closure 144 are disposed externally of a surface of the closure 144, as will be described in greater detail below. The method for collecting a sample with the containing apparatus 140 is the same as the method used with the containing apparatus 50.

The closure 140 has a closure body 150 separated in two cylindrical portions 152 and 154 by a closure wall 155. The cylindrical portion 152 is provided with a thread region 156 extending outwardly from an exterior wall thereof. Similarly, the cylindrical portion 154 is provided with a thread region 158 extending outwardly from an exterior wall thereof. Both thread regions 156 and 158 are designed to complement the thread region 148 of the tube 142, thus allowing both portions 152 and 154 to be screwed onto the tube 142. The closure 140 has an exterior cylindrical wall 160 which covers the exterior portion of the tube 142 as shown. The closure 140 has a connector 162 which is integrally formed in the cylindrical portion 152 to receive the shaft 58 of the sample collection device 52.

It is contemplated that the closure 140 could be made of two or more separate parts connected together, instead of integrally formed as a single part as shown in FIG. 14.

FIGS. 15 and 16 illustrate alternative embodiments of closures which could be used with the containing apparatus 140. For simplicity, elements of these embodiments which are similar to those of the closure 144 have been labelled with the same reference numerals and will not be described again in detail.

FIG. 15 shows a closure 164 having the same features as the closure 144 except that the exterior cylindrical wall 160 has been removed. FIG. 16 shows a closure 166 having the same features as the closure 164 except that the closure wall 155 has also been removed.

Turning now to FIG. 17, a containing apparatus 200 will be described. The containing apparatus 200 includes the closure 10, two tubes 54A and 54B, and a sample collection device 52. The tubes 54A and 54B are similar to the tube 54 described above. It is contemplated that the tubes 54A and 54B could be identical or different, and that at least one of the tubes 54A and 54B could be replaced by a different type of container. The tube 54A is screwed to the portion 14 of the closure 10 and the tube 54B is screwed to the portion 16 of the closure 10. It is contemplated that any one of the closures 80, 82, 84, 86, 90, 100, and 132A to 132D could alternatively be used in the containing apparatus 200. It is also contemplated that the sample collection device 52 could be provided separately from the containing apparatus 200 (i.e. not preassembled to the closure 10). It is also contemplated that a sample collection device 52 could extend in each of the tubes 52 by using the closure 82 described above.

A substance, such as liquid 62 or another substance, can be provide in only one of the tubes 54A and 54B or in both tubes 54A and 54B. Alternatively, both tubes 54A and 54B could be empty. In one embodiment, the tube 54A is empty and is used to protect the sample collection device 52 prior to collecting the sample. In another embodiment, the tube 54A includes a solution which can be used to prepare or clean the site where the sample is to be collected.

To use the containing apparatus 200, the portion 14 of the closure is first unscrewed from the closure 10. The user then holds the tube 54B as a handle or collection wand and collects the sample as previously described. The user then unscrews the closure 10 from the tube 54B. Finally, the user inserts the sample collection device in the tube 54B and screws the portion 14 of the closure 10 to the tube 54B. Optionally, the user may then screw the portion 16 of the closure 10 to the tube 54A.

Figure 18:
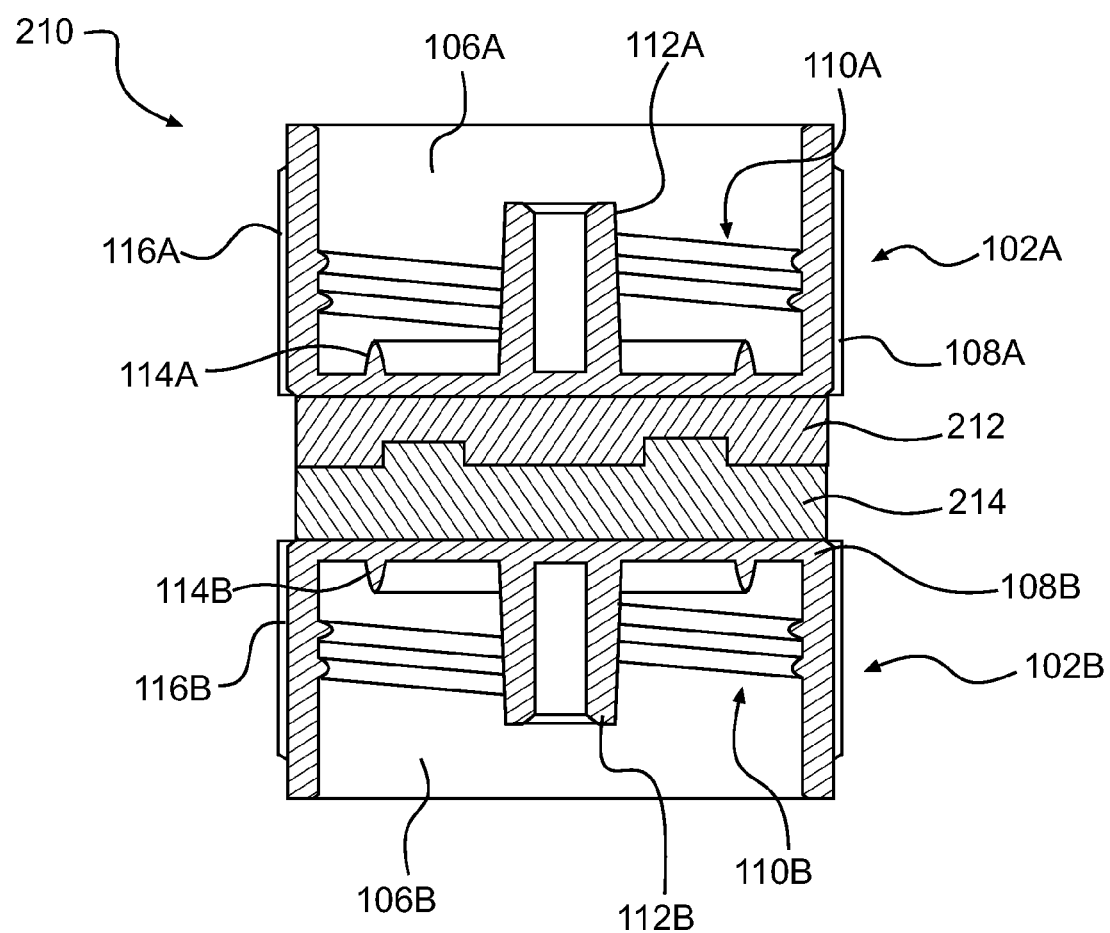
FIG. 18 is a cross-section of another alternative embodiment of a closure.

FIG. 18 shows a cross-section of a closure 210 that could be used in any one of the containing apparatuses 50, 70, and 200 described above. The closure 210 is made of two closure bodies 102A and 102B and two connectors 212 and 214. The two closure bodies 102A and 102B have structures similar to the closure body 102 described above. As such, elements of the two closure bodies 102A and 102B which correspond to those of the closure 102 have been labelled with the same reference numerals with the addition of the suffix A or B, as the case may be, and will not be described again in detail. Although shown as being identical, it is contemplated that the two closure bodies 102A and 102B could be different as in the closure 100 described above. The closure bodies 102A and 102B are injection molded, although other manufacturing methods are contemplated. Since they are identical, the same mold can be used to make both closure bodies 102A and 102B. However, when the closure body 102A is molded, the connector 212 is inserted in the mold so as to be connected to the top 108A. Similarly, when the closure body 102B is molded, the connector 214 is inserted in the mold so as to be connected to the top 108B. It is contemplated that the connectors 212 and 214 could be connected to their respective tops 108A and 108B after the molding of the closure bodies 102A and 102B. For example, the connectors 212 and 214 could be bonded to their respective tops 108A and 108B. As can be seen, the connectors 212 and 214 each form a part of a male-female connector. To assemble the closure 210, the male portion of the connector 214 is inserted in the female portion of the connector 212, thus connecting the closure body 102A to the closure body 102B via a friction fit. It is contemplated that the connectors 212 and 214 could be designed so as to provide a different type of connection therebetween. For example, the connectors 212 and 214 could each form a part of a pressure fastener (i.e. a snap).

It is contemplated that in at least some of the embodiments of the closures described above that the thread regions could be replaced by another type of engagement means and that the container would be provided with a complementary engagement means. It is also contemplated that in at least some of the embodiments of the closures described above that the thread regions could be omitted and that the closure would be connected to the container due to an interference or transition fit between the closure and the container.

Modifications and improvements to the above-described embodiments of the present invention may become apparent to those skilled in the art. The foregoing description is intended to be exemplary rather than limiting. The scope of the present invention is therefore intended to be limited solely by the scope of the appended claims.

What is claimed is:

1. A closure for a container, the container having an opened end, the closure comprising:
    a closure body, the closure body comprising:
        a first cylindrical portion; and
        a second cylindrical portion opposite the first portion; and
        a closure wall separating the first portion from the second portion; and
    a connector disposed within the closure body, the connector comprising a hollow connector body extending through and protruding from at least one side of the closure wall, the connector being adapted to connect one of a sample collection device and an applicator to the closure in at least one of the first and second portions, wherein the hollow connector body has an opened end for receiving a shaft of the one of the sample collection device and the applicator and a closed end.

2. The closure of claim 1, wherein at least one of the first cylindrical portion and the second cylindrical portion has a thread region complementary to a thread region of the container located near the opened end of the container for engagement therewith.

3. The closure of claim 2, wherein the first cylindrical portion has a first thread region; and the second cylindrical portion has a second thread region; and
    the first and second thread regions are complementary to a thread region of the container located near the opened end of the container for engagement therewith.

4. The closure of claim 3, wherein the first portion has a first cylindrical interior wall; and
    wherein the second portion has a second cylindrical interior wall.

5. The closure of claim 3, wherein the first thread region extends inwardly from the first cylindrical interior wall; and
    wherein the second thread region extends inwardly from the second cylindrical interior wall.

6. The closure of claim 4, wherein the connector extends in a space defined by the first cylindrical interior wall; and wherein the closure body further comprises:
    a first wiper seal having a circular cross-section extending from the closure wall in the space defined by the first cylindrical interior wall, the first wiper seal being disposed between the connector and the first cylindrical interior wall in a radial direction of the closure body; and
    a second wiper seal having a circular cross-section extending from the closure wall in a space defined by the second cylindrical interior wall.

7. The closure of claim 1, wherein an interior of the hollow connector body tapers from the opened end to the closed end.

8. The closure of claim 1, wherein the connector is a first connector adapted to connect one of a first sample collection device and a first applicator to the closure; and the closure further comprising a second connector disposed in at least one of the first and second portions, the second connector adapted to connect one of a second sample collection device and a second applicator to the closure.

9. The closure of claim 8, wherein the one of a first sample collection device and a first applicator and the one of a second sample collection device and a second applicator both extend from a same one of the first and second cylindrical portions of the closure.

10. The closure of claim 8, wherein the one of a first sample collection device and a first applicator extends from the first cylindrical portion of the closure and the one of a second sample collection device and a second applicator extends from the second cylindrical portion of the closure.

11. The closure of claim 1, further comprising a sheath connected to the closure body and extending externally thereof.

12. The closure of claim 1, wherein the closure body is made of at least one of polypropylene, low-density polyethylene (LDPE), medium-density polyethylene (MDPE), high-density polyethylene (HDPE), polyethylene, polyvinyl chloride (PVC), polycarbonate, and thermoplastic elastomer (TPE).

13. The closure of claim 1, wherein the hollow connector body has a cross-sectional shape corresponding to the cross-sectional shape of the shaft of the one of the sample connector and the applicator.

14. The closure of claim 1, wherein the one of the sample collection device and the applicator is integrally formed with said closure.

15. A method of collecting a sample comprising the steps of:
    providing a containing apparatus, the containing apparatus including a container and a closure, the closure comprising:
        a closure body, the closure body comprising:
            a first cylindrical portion;
            a second cylindrical portion opposite the first portion; and
            a closure wall separating the first portion from the second portion; and
        a connector disposed within the closure body, the connector comprising a hollow connector body extending through and protruding from at least one side of the closure wall, the connector connecting a sample collection device to the closure in the second portion, wherein the hollow connector body has an opened end receiving a shaft of the sample connector and a closed end;
    applying the sample collection device to the sample to be collected by holding the container, the container having the first portion of the closure screwed on an opened end thereof;
    unscrewing the first portion of the closure from the opened end of the container;
    inserting the sample collection device in the container; and
    screwing the second portion of the closure to the opened end of the container.

16. A containing apparatus comprising:
    a container having an opened end and a thread region near the opened end;
    the closure of claim 1, the closure being selectively connectable to the opened end of the container in a first configuration and in a second configuration, the connector being disposed in the first portion of the closure body; and
    one of a sample collection device and an applicator connected to the connector and extending from the first portion of the closure body away from the second portion of the closure body;
    wherein when the closure is connected to the opened end of the container in the first configuration:

the second thread region of the closure engages the thread region of the container, and the one of the sample collection device and the applicator is disposed outside the container and extends away therefrom; and wherein when the closure is connected to the opened end of the container in the second configuration:

the first thread region of the closure engages the thread region of the container, and the one of the sample collection device and the applicator is disposed inside the container.

17. The containing apparatus of claim 16, wherein the container is one of a tube and a vial.

18. The containing apparatus of claim 16, wherein the one of the sample collection device and the applicator is the sample collection device;

wherein the sample collection device includes a shaft and a sample collection implement; and wherein the shaft has a first end connected to the connector and a second end connected to the sample collection implement.

19. The containing apparatus of claim 18, wherein the sample collection implement is one of a swab, a sponge, a brush, a spatula, a loop, a scraper, a spoon, a scoop, a depressor, a capillary tube, a tissue punch, an absorbent solid matrix, and a large bore needle.

20. The containing apparatus of claim 16, further comprising a substance in the container.

21. The containing apparatus of claim 20, wherein the substance is a biomolecule-stabilizing composition.

22. The containing apparatus of claim 21, wherein the biomolecule-stabilizing composition is a nucleic acid-stabilizing composition.

23. The containing apparatus of claim 21, wherein when the closure is connected to the opened end of the container a fluid-tight seal is formed between the container and the closure.

24. The containing apparatus of claim 16, further comprising an extension selectively connected to an end of the container opposite the one of the sample collection device and the applicator.

25. A closure for a container, the container having an opened end, the closure comprising:

a first closure body, the first closure body comprising:
a first cylindrical wall; and
a first top connected to an end of the first cylindrical wall;

a second closure body, the second closure body comprising:
a second cylindrical wall; and
a second top connected to an end of the second cylindrical wall; and a connector disposed in at least one of the first and second closure bodies, the connector comprising a hollow connector body extending through and protruding from one of the first top and the second top and being adapted to connect one of a sample collection device and an applicator to the closure, wherein the hollow connector body has an opened end for receiving a shaft of the one of the sample connector and the applicator and a closed end, the first top being connected to the second top such that the first and second closure bodies are generally coaxial.

26. The closure of claim 25, wherein the connector extends through the first top.

27. A containing apparatus comprising:

a container having an opened end and a thread region near the opened end;

a closure of claim 25, the closure being selectively connectable to the opened end of the container in a first configuration and in a second configuration, the connector being disposed in the first closure body; and one of a sample collection device and an applicator connected to the connector and extending from the first closure body away from the second closure body;

wherein when the closure is connected to the opened end of the container in the first configuration:

the second thread region of the second closure body engages the thread region of the container, and the one of the sample collection device and the container is disposed outside the container and extends away therefrom; and wherein when the closure is connected to the opened end of the container in the second configuration:

the first thread region of the first closure body engages the thread region of the container, and the one of the sample collection device and the applicator is disposed inside the container.

28. A method of collecting a sample using the containing apparatus of claim 16 or 27, comprising:

connecting the sample collection device to the closure by inserting the shaft of the sample collection device into the hollow connector body of the closure;

applying the sample collection device to the sample to be collected by holding the container, the container having the first portion of the closure screwed on an opened end thereof;

unscrewing the first portion of the closure from the opened end of the container;

inserting the sample collection device in the container; and screwing the second portion of the closure to the opened end of the container.

29. The method of claim 28, wherein inserting the sample collection device in the container includes immersing an end of the sample collection device in a substance contained in the container.

30. The method of claim 28, wherein the containing apparatus includes a sheath connected to the closure and extending externally thereof, the method further comprising:

placing the sheath at least in part over the container prior to applying the sample collection device.

31. The closure of claim 25, wherein the first closure body further comprises a first thread region extending inwardly from the first cylindrical wall, the first thread region being complementary to a thread region of the container located near the opened end of the container for engagement therewith; and wherein the second closure body further comprises a second thread region extending inwardly from the second cylindrical wall, the second thread region being complementary to the thread region of the container for engagement therewith.

* * * * *